United States Patent
Chaturvedi et al.

(10) Patent No.: US 11,969,258 B2
(45) Date of Patent: Apr. 30, 2024

(54) SYSTEM AND METHOD FOR DETERMINING VESSEL SIZE

(71) Applicant: Briteseed LLC, Chicago, IL (US)

(72) Inventors: Amal Chaturvedi, San Jose, CA (US); Hariharan Subramanian, Northbrook, IL (US); Jonathan Gunn, Chicago, IL (US); Mayank Vijayvergia, Chicago, IL (US); Shetha Shukair, Chicago, IL (US); Paul Le Rolland, Mountain View, CA (US)

(73) Assignee: Briteseed, LLC, Chicago, IL (US)

( * ) Notice: Subject to any disclaimer, the term of this patent is extended or adjusted under 35 U.S.C. 154(b) by 957 days.

(21) Appl. No.: 16/932,494

(22) Filed: Jul. 17, 2020

(65) Prior Publication Data

US 2020/0345297 A1  Nov. 5, 2020

Related U.S. Application Data

(63) Continuation of application No. 15/764,527, filed as application No. PCT/US2016/055910 on Oct. 7, 2016, now Pat. No. 10,716,508.
(Continued)

(51) Int. Cl.
*A61B 5/05* (2021.01)
*A61B 5/00* (2006.01)
(Continued)

(52) U.S. Cl.
CPC ............ *A61B 5/489* (2013.01); *A61B 5/0084* (2013.01); *A61B 5/02007* (2013.01);
(Continued)

(58) Field of Classification Search
CPC ... A61B 5/489; A61B 5/0084; A61B 5/02007; A61B 5/1076; A61B 5/7207;
(Continued)

(56) References Cited

U.S. PATENT DOCUMENTS 5,129,400 A    7/1992  Makino et al.
5,259,761 A    11/1993 Schnettler et al.
(Continued)

FOREIGN PATENT DOCUMENTS

EP    2353534    8/2011
GB    1445678    8/1976
(Continued)

OTHER PUBLICATIONS

Akl et al., Performance Assessment of an Opto-Fluidic Phantom Mimicking Porcine Liver Parenchyma, J. Bio. Optics, vol. 17(7) 077008-1 to 077008-9 (Jul. 2012).
(Continued)

*Primary Examiner* — Joel F Brutus
(74) *Attorney, Agent, or Firm* — Cook Alex Ltd.

(57) ABSTRACT

A surgical system includes at least one light emitter generating light at a first intensity and an array of light sensors including a least one row of light sensors, individual light sensors in the row of light sensors adapted to generate a signal including a non-pulsatile component. The system also includes a controller coupled to the array of light sensors, the controller including an analyzer to determine the magnitudes of the non-pulsatile components at the individual light sensors in the row of light sensors, to determine if the non-pulsatile component transitions from a higher magnitude to a lower magnitude and from a lower magnitude to a higher magnitude, and if so, to determine if the first intensity should be changed to a second intensity.

19 Claims, 12 Drawing Sheets

Related U.S. Application Data

(60) Provisional application No. 62/239,152, filed on Oct. 8, 2015.

(51) Int. Cl.
| | |
|---|---|
| *A61B 5/02* | (2006.01) |
| *A61B 5/107* | (2006.01) |
| *A61B 18/08* | (2006.01) |
| *A61B 34/00* | (2016.01) |
| *A61B 17/00* | (2006.01) |
| *A61B 18/00* | (2006.01) |

(52) U.S. Cl.
CPC .......... *A61B 5/1076* (2013.01); *A61B 5/7207* (2013.01); *A61B 18/085* (2013.01); *A61B 34/76* (2016.02); *A61B 2017/00057* (2013.01); *A61B 2017/00123* (2013.01); *A61B 2018/00595* (2013.01); *A61B 2018/00642* (2013.01); *A61B 2505/05* (2013.01)

(58) Field of Classification Search
CPC ............ A61B 18/085; A61B 18/00595; A61B 18/00642; A61B 2017/00057; A61B 2017/00123
See application file for complete search history.

(56) References Cited

U.S. PATENT DOCUMENTS

| | | |
|---|---|---|
| 5,762,609 A | 6/1998 | Benaron et al. |
| 5,769,791 A | 6/1998 | Benaron et al. |
| 5,772,597 A | 6/1998 | Goldberger et al. |
| 5,785,658 A | 7/1998 | Benaron et al. |
| 5,807,261 A | 9/1998 | Benaron et al. |
| 5,987,346 A | 11/1999 | Benaron et al. |
| 6,178,340 B1 | 1/2001 | Svetliza |
| 6,374,128 B1 | 4/2002 | Toida et al. |
| 6,569,104 B2 | 5/2003 | Ono et al. |
| 6,594,518 B1 | 7/2003 | Benaron et al. |
| 6,922,577 B2 | 7/2005 | Nakashima et al. |
| 7,006,861 B2 | 2/2006 | Flock et al. |
| 7,112,201 B2 | 9/2006 | Truckai et al. |
| 7,235,072 B2 | 6/2007 | Sartor et al. |
| 7,515,265 B2 | 4/2009 | Alfano et al. |
| 7,740,591 B1 | 6/2010 | Starr et al. |
| 7,749,217 B2 | 7/2010 | Podhajsky |
| 7,904,138 B2 | 3/2011 | Goldman et al. |
| 7,983,738 B2 | 7/2011 | Goldman et al. |
| 8,058,771 B2 | 11/2011 | Giordano et al. |
| 8,073,531 B2 | 12/2011 | Goldman et al. |
| 8,118,206 B2 | 2/2012 | Zand et al. |
| 8,123,745 B2 | 2/2012 | Beeckler et al. |
| 8,150,500 B2 | 4/2012 | Goldman et al. |
| 8,185,177 B2 | 5/2012 | Numada et al. |
| 8,244,333 B2 | 8/2012 | Wood et al. |
| 8,255,040 B2 | 8/2012 | Goldman et al. |
| 8,295,904 B2 | 10/2012 | Goldman et al. |
| 8,380,291 B2 | 2/2013 | Wood et al. |
| 8,391,960 B2 | 3/2013 | Wood et al. |
| 8,417,306 B2 | 4/2013 | Cheng |
| 8,463,364 B2 | 6/2013 | Wood et al. |
| 8,467,857 B2 | 6/2013 | Kim et al. |
| 8,478,386 B2 | 7/2013 | Goldman et al. |
| 8,483,805 B2 | 7/2013 | Takenoshita et al. |
| 8,483,819 B2 | 7/2013 | Choi et al. |
| 8,489,178 B2 | 7/2013 | Wood et al. |
| 8,586,924 B2 | 11/2013 | Demos |
| 8,591,425 B2 | 11/2013 | Owen et al. |
| 8,649,568 B2 | 2/2014 | Sato |
| 8,649,848 B2 | 2/2014 | Crane et al. |
| 8,682,418 B2 | 3/2014 | Tanaka |
| 8,706,200 B2 | 4/2014 | Goldman et al. |
| 8,712,498 B2 | 4/2014 | Goldman et al. |
| 8,750,970 B2 | 6/2014 | Goldman et al. |
| 8,792,967 B2 | 7/2014 | Sato |
| 8,818,493 B2 | 8/2014 | Goldman et al. |
| 8,820,931 B2 | 9/2014 | Walsh et al. |
| 8,838,210 B2 | 9/2014 | Wood et al. |
| 9,526,921 B2 | 12/2016 | Kimball et al. |
| 2002/0169381 A1 | 11/2002 | Asada et al. |
| 2003/0036685 A1 | 2/2003 | Goodman |
| 2003/0036751 A1 | 2/2003 | Anderson et al. |
| 2003/0120306 A1 | 6/2003 | Burbank et al. |
| 2004/0111085 A1 | 6/2004 | Singh |
| 2004/0116969 A1 | 6/2004 | Owen et al. |
| 2005/0143662 A1 | 6/2005 | Marchitto et al. |
| 2005/0180620 A1 | 8/2005 | Takiguchi |
| 2006/0020212 A1 | 1/2006 | Xu et al. |
| 2006/0052850 A1 | 3/2006 | Darmos et al. |
| 2006/0100523 A1 | 5/2006 | Ogle et al. |
| 2006/0129037 A1 | 6/2006 | Kaufman et al. |
| 2006/0155194 A1 | 7/2006 | Marcotte et al. |
| 2007/0038118 A1 | 2/2007 | DePue et al. |
| 2008/0058621 A1 | 3/2008 | Melker et al. |
| 2009/0018414 A1 | 1/2009 | Toofan |
| 2009/0054908 A1 | 2/2009 | Zand et al. |
| 2009/0112071 A1 | 4/2009 | LaBoeuf et al. |
| 2010/0222786 A1 | 9/2010 | Kassab |
| 2010/0249763 A1 | 9/2010 | Larson et al. |
| 2011/0021925 A1 | 1/2011 | Wood et al. |
| 2011/0245685 A1 | 10/2011 | Murata et al. |
| 2012/0016362 A1 | 1/2012 | Heinrich et al. |
| 2012/0046555 A1 | 2/2012 | Takamatsu et al. |
| 2012/0143182 A1 | 6/2012 | Ullrich et al. |
| 2012/0172842 A1 | 7/2012 | Sela et al. |
| 2012/0296205 A1 | 11/2012 | Chernov et al. |
| 2012/0316448 A1* | 12/2012 | Gu ..................... A61B 5/02108 600/499 |
| 2013/0102905 A1 | 4/2013 | Goldman et al. |
| 2013/0226013 A1 | 8/2013 | McEwen et al. |
| 2013/0267874 A1 | 10/2013 | Marcotte et al. |
| 2014/0086459 A1 | 3/2014 | Pan et al. |
| 2014/0100455 A1 | 4/2014 | Goldman et al. |
| 2014/0155753 A1 | 6/2014 | McGuire, Jr. et al. |
| 2014/0194751 A1 | 7/2014 | Goldman et al. |
| 2014/0213863 A1* | 7/2014 | Loseu ..................... A61B 5/725 600/324 |
| 2014/0236019 A1 | 8/2014 | Rahum |
| 2014/0276088 A1 | 9/2014 | Drucker |
| 2014/0313482 A1 | 10/2014 | Shahidi et al. |
| 2015/0011896 A1 | 1/2015 | Yelin et al. |
| 2015/0051460 A1 | 2/2015 | Saxena et al. |
| 2015/0066000 A1 | 3/2015 | An et al. |
| 2015/0196240 A1 | 7/2015 | Nishimoto et al. |
| 2017/0181701 A1 | 6/2017 | Fehrenbacher et al. |
| 2018/0042522 A1 | 2/2018 | Subramanian et al. |
| 2018/0047167 A1 | 2/2018 | Xu et al. |
| 2018/0098705 A1 | 4/2018 | Chaturvedi et al. |

FOREIGN PATENT DOCUMENTS

| | | |
|---|---|---|
| JP | H10-005245 | 1/1998 |
| JP | 2001-112716 | 4/2001 |
| JP | 2003-019116 | 1/2003 |
| JP | 2006-130201 | 5/2006 |
| JP | 2008-194455 | 8/2008 |
| JP | 2010-046425 | 3/2010 |
| JP | 2010-081972 | 4/2010 |
| WO | WO98/27865 | 7/1998 |
| WO | WO2001/060427 | 8/2001 |
| WO | WO2003/039326 | 5/2003 |
| WO | WO2004/030527 | 4/2004 |
| WO | WO2005/091978 | 10/2005 |
| WO | WO2008/082992 | 7/2008 |
| WO | WO2009/144653 | 12/2009 |
| WO | WO2011/013132 | 2/2011 |
| WO | WO2012/158774 | 11/2012 |
| WO | WO2013/134411 | 9/2013 |
| WO | WO2014/050945 | 4/2014 |
| WO | WO2014/194317 | 12/2014 |
| WO | WO2015/148504 | 10/2015 |
| WO | WO2016/134327 | 8/2016 |
| WO | WO2016/134330 | 8/2016 |

(56) References Cited

FOREIGN PATENT DOCUMENTS

| WO | WO2017/139624 | 8/2017 |
|---|---|---|
| WO | WO2017/139642 | 8/2017 |
| WO | WO2018/044722 | 3/2018 |

OTHER PUBLICATIONS

Comtois et al., A Comparative Evaluation of Adaptive Noise Cancellation Algorithms for Minimizing Motion Artifacts in a Forehead-Mounted Wearable Pulse Oximeter, Conf. Proc. IEEE Eng. Med. Biol. Soc., 1528-31 (2007).

Figueiras et al., Self-Mixing Microprobe for Monitoring Microvascular Perfusion in Rat Brain, Med. Bio. Eng'r Computing 51:103-112 (Oct. 12, 2012).

Hammer et al., A Simple Algorithm for In Vivo Ocular Fundus Oximetry Compensating for Non-Haemoglobin Absorption and Scattering, Phys. Med. Bio. vol. 47, N233-N238 (Aug. 21, 2002).

Ibey et al., Processing of Pulse Oximeter Signals Using Adaptive Filtering and Autocorrelation to Isolate Perfusion and Oxygenation Components, Proc SPIE, vol. 5702, 54-60 (2005).

Li et al., Pulsation-Resolved Deep Tissue Dynamics Measured with Diffusing-Wave Spectroscopy, Optics Express, vol. 14, No. 17, 7841-7851 (Aug. 21, 2006).

Mendelson et al., In-vitro Evaluation of a Dual Oxygen Saturation/Hematocrit Intravascular Fiberoptic Catheter, Biomed Instrum. Technol. 24(3):199-206 (May/Jun. 1990).

Phelps et al., Rapid Ratiometric Determination of Hemoglobin Concentration using UV-VIS Diffuse Reflectance at Isobestic Wavelengths, Optics Express, vol. 18, No. 18, 18779-18792 (Aug. 30, 2010).

Subramanian, Real Time Perfusion and Oxygenation Monitoring in an Implantable Optical Sensor, Thesis Texas A&M Univ. (Dec. 2004).

Subramanian, Real-Time Separation of Perfusion and Oxygenation Signals for an Implantable Sensor Using Adaptive Filtering, IEEE Trans. Bio. Eng'g, vol. 52, No. 12, 2016-2023 (Dec. 2005).

Subramanian, An Autocorrelation-Based Time Domain Analysis Technique for Monitoring Perfusion and Oxygenation in Transplanted Organs, IEEE Trans. Bio. Eng'g, vol. 52, No. 7, 1355-1358 (Jul. 2005).

International Search Report and Written Opinion, counterpart PCT application PCT/US2016/055910 (dated Jan. 17, 2017) (17 pages).

Search Report, counterpart Japanese App. No. 2018-517573, with English translation (dated Sep. 3, 2020) (23 pages).

Notice of Reasons for Refusal, counterpart Japanese App. No. 2018-517573, with English translation (dated Sep. 8, 2020) (15 pages).

Search Report and English-language machine translation, counterpart Japanese App. No. 2022-064049 (dated Jan. 31, 2023) (23 pages).

Notice of Reasons for Refusal and English-language machine translation, counterpart Japanese App. No. 2022-064049 (dated Feb. 7, 2023) (10 pages).

\* cited by examiner

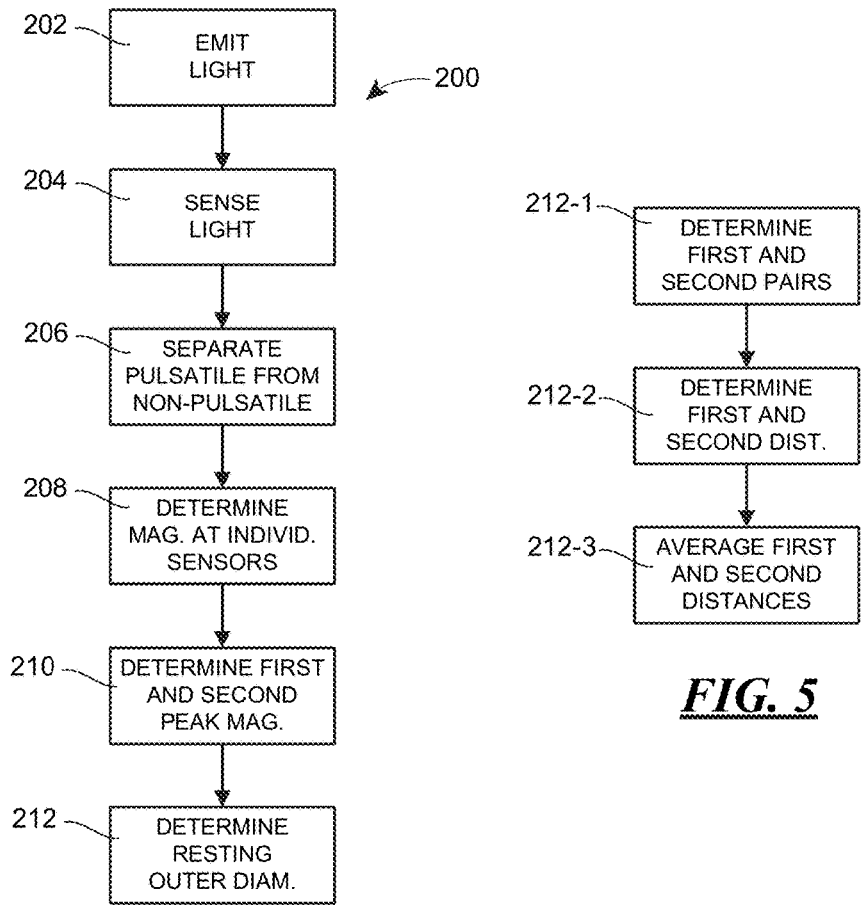
*FIG. 4*
*FIG. 5*
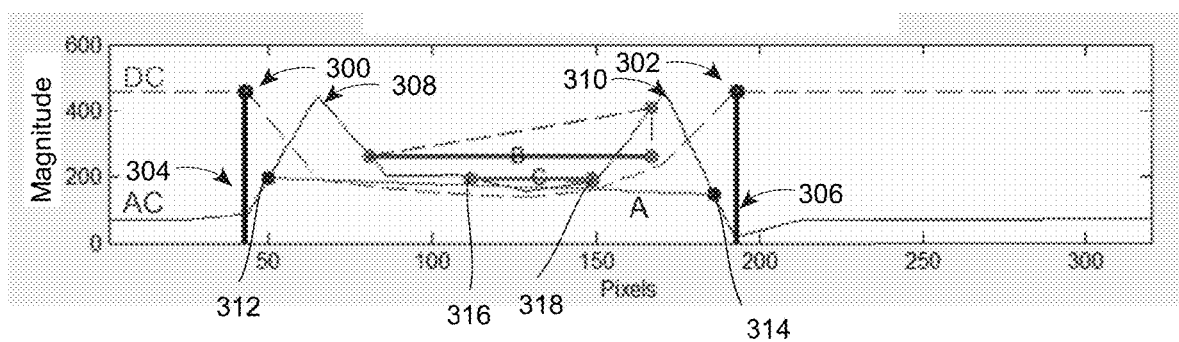
*FIG. 6*

SYSTEM AND METHOD FOR DETERMINING VESSEL SIZE

The present application is a continuation of U.S. patent application Ser. No. 15/764,527, which is a U.S. National Stage of PCT International Pat. App. No. PCT/US2016/055910, filed Oct. 7, 2016, which claims the benefit of U.S. Provisional Pat. App. No. 62/239,152, filed Oct. 8, 2015, all of which are hereby incorporated herein by reference.

BACKGROUND

This patent is directed to a system and method for determining the size of a vessel, such as a blood vessel, and in particular to a system and method using the light transmitted to a sensor array that includes a pulsating component.

Systems and methods that identify artifacts, and in particular vessels, in the surgical field during a surgical procedure provide valuable information to the surgeon or surgical team. U.S. hospitals lose billions of dollars annually in unreimbursable costs because of inadvertent vascular damage during surgery. In addition, the involved patients face a mortality rate of up to 32%, and likely will require corrective procedures and remain in the hospital for an additional nine days, resulting in tens, if not hundreds, of thousands of dollars in added costs of care. Consequently, there is this significant value to be obtained from methods and systems that permit accurate determination of the presence of vessels, such as blood vessels, in the surgical field, such that these costs may be reduced or avoided.

Systems and methods that provide information regarding the presence of blood vessels in the surgical field are particularly important during minimally-invasive surgical procedures. Traditionally, surgeons have relied upon tactile sensation during surgical procedures both to identify blood vessels and to avoid inadvertent damage to these vessels. Because of the shift towards minimally-invasive procedures, including laparoscopic and robotic surgeries, surgeons have lost the ability to use direct visualization and the sense of touch to make determinations as to the presence of blood vessels in the surgical field. Consequently, surgeons must make the determination whether blood vessels are present in the surgical field based primarily on convention and experience. Unfortunately, anatomical irregularities frequently occur because of congenital anomalies, scarring from prior surgeries, and body habitus (e.g., obesity).

While the ability to determine the presence or absence of a vessel within the surgical field provides valuable advantages to the surgeon or surgical team and is of particular importance for minimally-invasive procedures where direct visualization and tactile methods of identification have been lost, the ability to characterize the identified vasculature provides additional important advantages. For example, it would be advantageous to provide information relating to the size of the vessel, such as the inner or outer diameter of the vessel. Size information is particularly relevant as the Food and Drug Administration presently approves, for example, thermal ligature devices to seal and cut vessels within a given size range, typically less than 7 mm in diameter for most thermal ligature devices. If a thermal ligature device is used to seal a larger blood vessel, then the failure rate for a seal thus formed may be as high as 19%.

In addition, it would be preferable to provide this information with minimal delay between vessel detection and vessel analysis, such that the information may be characterized as real-time. If considerable time is required for analysis, then at a minimum this delay will increase the time required to perform the procedure. In addition, the delay may increase surgeon fatigue, because the surgeon will be required to move at a deliberate pace to compensate for the delay between motion of the instrument and delivery of the information. Such delays may in fact hinder adoption of the system, even if the information provided reduces the risk of vascular injury.

Further, it would be advantageous to detect and analyze the vasculature without the need to use a contrast medium or agent. While the use of a contrast agent to identify vasculature has become conventional, the use of the agent still adds to the complexity of the procedure. The use of the agent may require additional equipment that would not otherwise be required, and increase the medical waste generated by the procedure. Further, the use of the contrast agent adds a risk of adverse reaction by the patient.

As set forth in more detail below, the present disclosure describes a surgical system including a system and method for determining vessel size embodying advantageous alternatives to the existing methods, which may provide for improved identification for avoidance or isolation of the vessel.

SUMMARY

According to an aspect of the present disclosure, a surgical system used to determine a size of a vessel within a region proximate to a working end of a surgical instrument is provided. The system includes at least one light emitter disposed at the working end of the surgical instrument, the at least one light emitter generating light at a first intensity, and an array of light sensors disposed at the working end of the surgical instrument opposite the at least one light emitter, the array of light sensors including a least one row of light sensors, individual light sensors in the row of light sensors adapted to generate a signal including a non-pulsatile component. The system also includes a controller coupled to the array of light sensors, the controller including an analyzer to determine the magnitudes of the non-pulsatile components at the individual light sensors in the row of light sensors, to determine if the non-pulsatile component transitions from a higher magnitude to a lower magnitude and from a lower magnitude to a higher magnitude, and if the non-pulsatile component transitions from a higher magnitude to a lower magnitude and from a lower magnitude to a higher magnitude, to determine if the first intensity should be changed to a second intensity.

According to another aspect of the present disclosure, a method of determining if a size of a vessel within a region proximate to a working end of a surgical instrument is provided. The method includes emitting light at the working end of the surgical instrument, the light emitted at a first intensity, sensing light at the working end of the surgical instrument at an array of light sensors including at least one row of light sensors, and generating a signal including a non-pulsatile component for individual sensors along the row of light sensors. The method further includes determining the magnitudes of the non-pulsatile components at the individual light sensors in the row of light sensors, determining if the non-pulsatile component transitions from a higher magnitude to a lower magnitude and from a lower magnitude to a higher magnitude, and if the non-pulsatile component transitions from a higher magnitude to a lower magnitude and from a lower magnitude to a higher magnitude, determining if the first intensity should be changed to a second intensity.

According to a further aspect of the present disclosure, a surgical system used to determine a size of a vessel within a region proximate to a working end of a surgical instrument is provided. The system includes at least one light emitter disposed at the working end of the surgical instrument, and an array of light sensors disposed at the working end of the surgical instrument opposite the at least one light emitter, the array of light sensors including a least one row of light sensors, individual light sensors in the row of light sensors adapted to generate a signal including a non-pulsatile component. The system also includes a controller coupled to the array of light sensors, the controller including an analyzer to determine the magnitudes of the non-pulsatile components at the individual light sensors in the row of light sensors, to determine a pair of positions corresponding to a first transition in the non-pulsatile component from a higher magnitude to a lower magnitude and a second transition in the non-pulsatile component from a lower magnitude to a higher magnitude, and to determine a resting outer diameter of the vessel based on a symmetrical non-pulsatile profile according to the pair of positions.

BRIEF DESCRIPTION OF THE DRAWINGS

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

FIG. 4 is a flow diagram of a method according to an embodiment of the present disclosure, which method may be carried out using the system of FIG. 1;

FIG. 5 is a flow diagram of particular actions that may be performed as part of the method illustrated in FIG. 4;

FIG. 6 is a graph of the magnitudes of the pulsatile (AC) and non-pulsatile (DC) components for each of the elements (pixels) of a light sensor array, the graph being used to illustrate general concepts disclosed herein;

DETAILED DESCRIPTION OF VARIOUS EMBODIMENTS

A surgical system according to an embodiment of the present disclosure includes at least one light emitter, at least one light sensor, and a controller. The system may also include a surgical instrument as well.

The system determines a size of a vessel within a region proximate to a working end of the surgical instrument. In particular, it is believed that the system may be used to determine the size of a vessel within the region proximate to the working end of the surgical instrument regardless of the presence or the type of tissue surrounding the vessel. The embodiments of the system described below perform determinations relative to the presence and size of the vessel within the targeted region based on the light transmittance as determined by the light sensor, and thus the embodiments may appear facially similar to the technology used in transmissive pulse oximetry to determine the oxygen saturation (i.e., the percentage of blood hemoglobin that is loaded with oxygen). Careful consideration of the following disclosure will reveal that the disclosed system utilizes the light emitter(s) and light sensor(s) in conjunction with a controller (either in the form of unique circuitry or a uniquely programmed processor) to provide information regarding the presence and size of vessels that would not be provided by a pulse oximeter. Further, the disclosed embodiments include the use of a sensor array, the controller processing the pulsatile and non-pulsatile components of signals from that array to yield information regarding the diameter(s) of the vessel (e.g. the inner diameter or the resting outer diameter). Moreover, the disclosed technology may be utilized with vessels other than blood vessels, further separating the disclosed system and method from a transmissive pulse oximeter.

Figure 1:
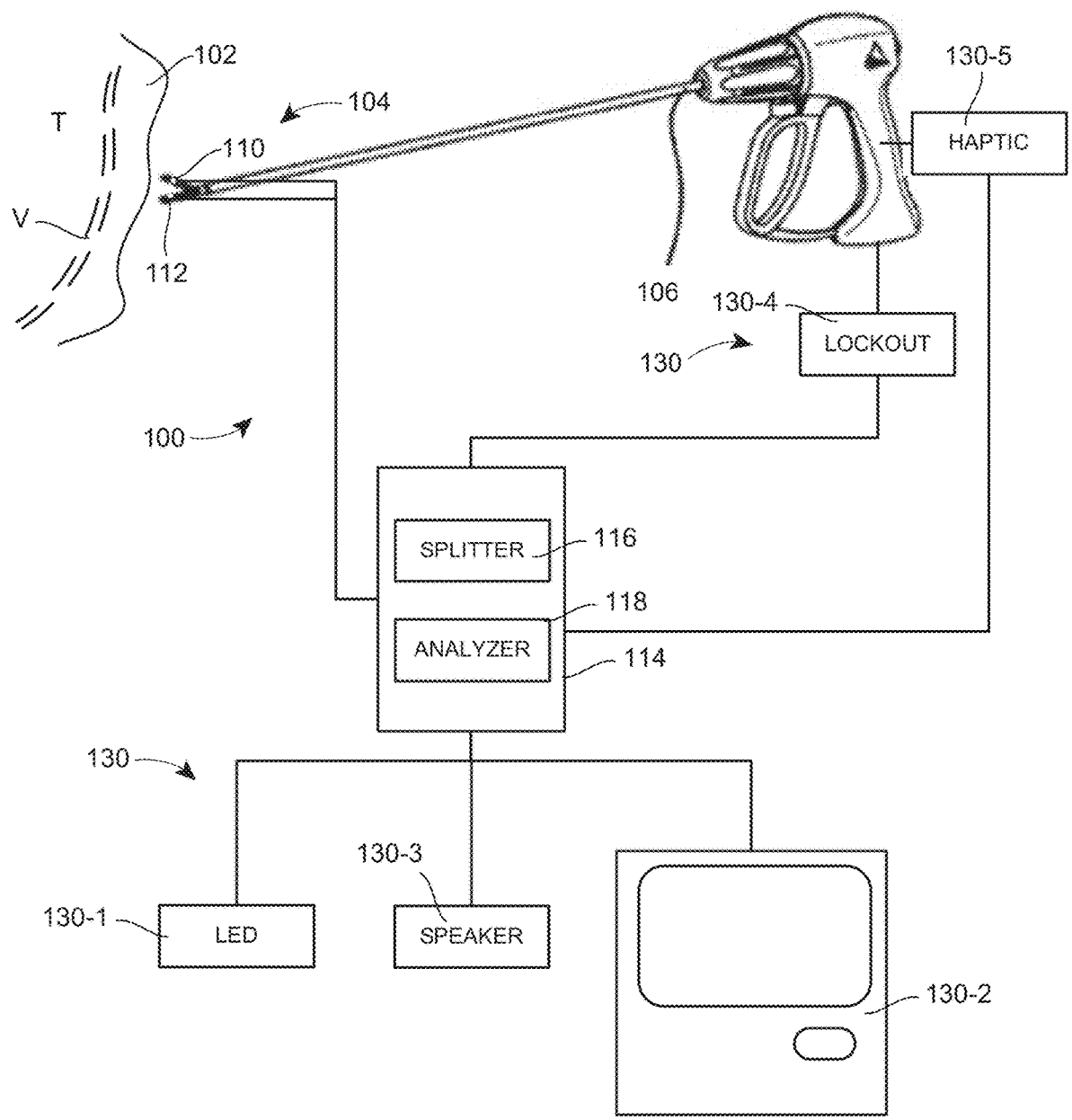
FIG. 1 is a schematic diagram of a surgical system according to an embodiment of the present disclosure.
Figure 2:
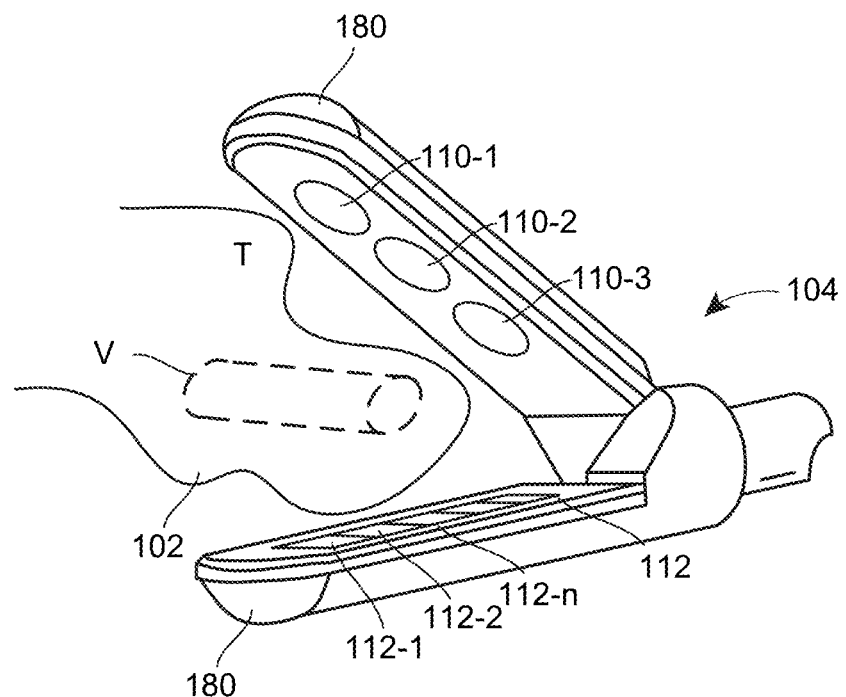
FIG. 2 is an enlarged, fragmentary view of the surgical instrument with light emitter and light sensors according to FIG. 1 with a section of a vessel illustrated as disposed between the light emitter and light sensors.

FIGS. 1 and 2 illustrate an embodiment of such a surgical system 100 used to determine a size (e.g., diameter) of a vessel, V, within a region 102 of tissue, T, proximate to a working end 104 of a surgical instrument 106. It will be understood that the vessel V may be connected to other vessels with the region 102 of tissue T, and in addition, the vessel V may extend beyond the region 102 so as to be in fluid communication with other organs (e.g., the heart) also found in the body of the patient. Furthermore, while the tissue T appears in FIGS. 1 and 2 to surround fully the vessel V (in terms of both circumference and length) to a particular depth, this need not be the case in all instances where the system 100 is used. For example, the tissue T may only partially surround the circumference of and/or only surround a section of the length of the vessel V, or the tissue T may overlie the vessel V in a very thin layer. As further non-limiting examples, the vessel V may be a blood vessel, and the tissue T may be connective tissue, adipose tissue or liver tissue.

The surgical system 100 includes at least one light emitter 110 (or simply the light emitter 110), at least one light sensor or detector 112 (or simply the light sensor 112), and a controller 114 coupled to the light emitter 110 and the light sensor 112. As noted above, the system 100 also may include the surgical instrument 106.

The light emitter 110 is disposed at the working end 104 of the surgical instrument 106. The light sensor 112 is also disposed at the working end 104 of the surgical instrument 106. As illustrated in FIGS. 1 and 2, the light sensor 112 may be disposed opposite the light emitter 110 because the light emitter 110 and the light sensor 112 are disposed on opposing elements of the surgical instrument 106, as explained in detail below.

The light emitter 110 is adapted to emit light of at least one wavelength. For example, the light emitter 110 may emit light having a wavelength of 660 nm. This may be achieved with a single element, or a plurality of elements (which elements may be arranged or configured into an array, for example, as explained in detail below). In a similar fashion, the light sensor 112 is adapted to detect light at the at least one wavelength (e.g., 660 nm). According to the embodiments described herein, the light sensor 112 includes a plurality of elements, which elements are arranged or configured into an array.

According to certain embodiments, the light emitter 110 may be configured to emit light of at least two different wavelengths, and the light sensor 112 may be configured to detect light at the at least two different wavelengths. For example, the light emitter 110 may emit light of three wavelengths, while the light sensor may detect light of three wavelengths. As one example, the light emitter 110 may emit and the light sensor 112 may detect light in the visible range, light in the near-infrared range, and light in the infrared range. Specifically, the light emitter 110 may emit and the light sensor 112 may detect light at 660 nm, at 810 nm, and at 940 nm. Such an embodiment may be used, for example, to ensure optimal penetration of blood vessel V and the surrounding tissue T under in vivo conditions.

In particular, the light emitted at 810 nm may be used as a reference to remove any variations in the light output because of motion and/or blood perfusion. The 810 nm wavelength corresponds to the isobestic point, where the absorption for both oxygenated and deoxygenated hemoglobin is equal. Consequently, the absorption at this wavelength is independent of blood oxygenation and is only affected by the change in light transmittance because of motion and/or changes in perfusion.

As stated above, the light sensor may be in the form of an array of light sensors. In fact, the array of light sensors 112 further includes at least one row of light sensors (see FIG. 2); according to certain embodiments, the array 112 may include only a single row of light sensors, and the array 112 may be referred to in the alternative as a linear array. The at least one row of light sensors 112 includes a plurality of individual light sensors. The individual light sensors 112 may be disposed adjacent each other, or the light sensors may be spaced from each other. It may even be possible for the individual light sensors that define a row of light sensors to be separated from each other by light sensors that define a different row or column of the array. According to a particular embodiment, however, the array may comprise a charge coupled device (CCD), and in particular linear CCD imaging device comprising a plurality of pixels. As a further alternative, a CMOS sensor array may be used.

According to the embodiments of this disclosure, the individual light sensors 112 (e.g., pixels) are adapted to generate a signal comprising a first pulsatile component and a second non-pulsatile component. It will be recognized that the first pulsatile component may be an alternating current (AC) component of the signal, while the second non-pulsatile component may be a direct current (DC) component. Where the light sensor 112 is in the form of an array, such as a CCD array, the pulsatile and non-pulsatile information may be generated for each element of the array, or at least for each element of the array that defines the at least one row of the array.

As to the pulsatile component, it will be recognized that a blood vessel may be described as having a characteristic pulsation of approximately 60 pulses (or beats) per minute. While this may vary with the patient's age and condition, the range of pulsation is typically between 60 and 100 pulses (or beats) per minute. The light sensor 112 will produce a signal (that is passed to the controller 114) with a particular AC waveform that corresponds to the movement of the blood through the vessel. In particular, the AC waveform corresponds to the light absorption by the pulsatile blood flow within the vessel. On the other hand, the DC component corresponds principally to light absorption and scattering by the surrounding tissues.

In particular, it is believed that the elements of the light sensor array 112 disposed on the opposite side of the vessel V from the light emitter 110 will have a higher AC signal than those elements where the vessel V is not disposed between the light emitter 110 and the light sensor array 112, because the most marked fluctuations in the transmitted light will be caused by the vessel-associated pulsations. It is also believed that the elements of the array 112 disposed on the opposite side of the vessel V from the light emitter 110 will have a decreased DC signal compared to elements of the array 112 where the vessel V is not disposed between the light emitter 110 and the array 112.

Figure 3:
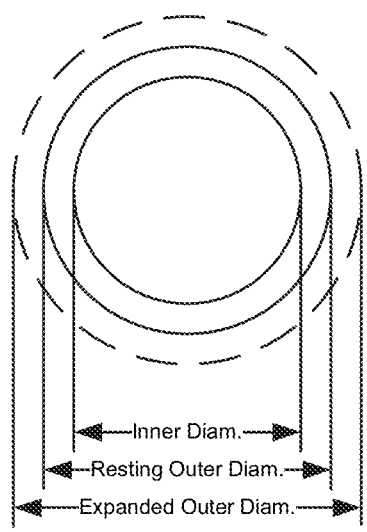
FIG. 3 is an enlarged cross-sectional view of a blood vessel with the wall expanding and contracting as blood flows through the vessel, with the change in outer diameter between a resting state and an expanded state exaggerated to better illustrate the changes in blood vessel outer diameter.

In fact, it is believed that particular regions of vessels, such as blood vessels, may undergo more pronounced pulsations that other regions, which differences are reflected in differences in the pulsatile component of the signal received from the array 112. More particularly and with reference to blood vessels as a non-limiting example, as the heart pumps blood through the body, the muscular arteries pulse to accommodate the volume of blood being directed through the body. As this occurs, the middle layer (or tunica media) of the vessel expands and contracts. The expansion and contraction of the tunica media results in a relatively more significant change to the outer diameter of the vessel than to the inner diameter of the vessel. It is believed that the relatively more significant change in outer diameter that occurs during the expansion and contraction of the vessel causes the greatest fluctuations in the AC signal (which, as mentioned above, is related to the pulsations) over time at the edges of the vessel, as the outer diameter oscillates between an expanded position A and a resting position B (see FIG. 3).

Thus, according to the disclosed embodiments, the controller 114 is coupled to the light sensor 112, and includes a splitter 116 to separate the first pulsatile component from the second non-pulsatile component for each element of the light sensor array 112. The controller 114 also includes an analyzer 118 to quantify the size of the vessel V within the region 102 proximate to the working end 104 of the surgical instrument 106 based on the pulsatile component. To display, indicate or otherwise convey the size of the vessel V within the region 102, the controller 114 may be coupled to an output device or indicator 130 (see FIG. 1), which may provide a visible, audible, tactile or other signal to the user of the instrument 106.

In particular, the analyzer 118 may determine the magnitudes of the pulsatile components at the individual light sensors in the row of light sensors. Further, the analyzer may determine a first peak magnitude and a second peak magnitude of the pulsatile components. The analyzer may make the determination as to the first and second peak magnitudes after first determining the locations of transitions in the pulsatile and non-pulsatile components of the signal between higher and lower magnitudes, as explained in detail below. In addition, the analyze 118 may determine a resting outer diameter of the vessel V based on the first and second peak magnitudes of the pulsatile components.

According to certain embodiments, the analyzer 118 may determine the resting outer diameter of the vessel V by determining a first pair of positions along the row of light sensors where the magnitudes of the pulsatile component are a percentage (e.g., between 25% and 75%, such as 50%) of the first (or second) peak magnitude, and a second pair of positions along the row of light sensors where the magnitudes of the pulsatile component are also the same percentage of the first (or second) peak magnitude, the second pair being disposed between the first pair of positions along the row of light sensors. The analyzer then determines a first distance between the first pair of positions and a second distance between the second pair of positions, and determines the resting outer diameter of the vessel as the average of the first and second distances. According to other embodiments, the analyzer 118 may instead use the inner pair of positions and a relationship between the inner and resting outer diameters. According to certain embodiments, the non-pulsatile component may be used instead of the pulsatile component.

According to certain embodiments, the splitter 116 and the analyzer 118 may be defined by one or more electrical circuit components. According to other embodiments, one or more processors (or simply, the processor) may be programmed to perform the actions of the splitter 116 and the analyzer 118. According to still further embodiments, the splitter 116 and the analyzer 118 may be defined in part by electrical circuit components and in part by a processor programmed to perform the actions of the splitter 116 and the analyzer 118.

For example, the splitter 116 may include or be defined by the processor programmed to separate the first pulsatile component from the second non-pulsatile component. Further, the analyzer 118 may include or be defined by the processor programmed to quantify the size of the vessel V within the region 102 proximate to the working end 104 of the surgical instrument 106 based on the first pulsatile component. The instructions by which the processor is programmed may be stored on a memory associated with the processor, which memory may include one or more tangible non-transitory computer readable memories, having computer executable instructions stored thereon, which when executed by the processor, may cause the one or more processors to carry out one or more actions.

In addition to the system 100, the present disclosure includes embodiments of a method 200 of determining if a size of a vessel V within a region 102 proximate to a working end 104 of a surgical instrument 106. The method 200 may be carried out, for example, using a system 100 as described above in regard to FIG. 1. As illustrated in FIG. 4, the method 200 of operating the system 100 includes emitting light at a working end of a surgical instrument at block 202 and sensing light at the working end of the surgical instrument at an array of light sensors comprising at least one row of light sensors at block 204. As explained above, the light emitted may include light of at least two different wavelengths, and the sensing step may thus include sensing light of at least two different wavelengths. As also noted above, three different wavelengths of light may be used, and for example in the visible range and the near-infrared range. According to one embodiment, the light used may have wavelengths of 660 nm, 810 nm, and 940 nm.

The method 200 continues at block 206 wherein a pulsatile component is separated from a non-pulsatile component for individual sensors along the row of light sensors. The method 200 also includes determining the magnitudes of the pulsatile components at the individual light sensors in the row of light sensors at block 208, determining a first peak magnitude and second peak magnitude of the pulsatile components at block 210, and determining a resting outer diameter of the vessel based on the first and second peak magnitudes of the pulsatile components at block 212.

More particular, as illustrated in FIG. 5, the block 212 of the method 200 of FIG. 4 may include one or more actions. In particular, as illustrated in FIG. 5, the action of block 212 may include determining a first pair and a second pair of positions along the row of light sensors at block 212-1, where the magnitudes of the pulsatile component of the first and second pair of positions are a percentage of the first (or second) peak magnitude. The second pair of positions is disposed between the first pair of positions, as will be discussed relative to FIG. 6 below. In addition, the action of block 212 may include determining a first distance between the first pair of positions and a second distance between the second pair of positions at block 212-2, and determining the resting outer diameter of the vessel V as the average of the first and second distances at block 212-3.

To illustrate further the method 200 of operation of the system 100, as illustrated in FIGS. 4 and 5, a plot is provided in FIG. 6. In particular, FIG. 6 is a simulated plot of the magnitude of the pulsatile (AC) component for each element of a light sensor array and a plot of the magnitude of the non-pulsatile (DC) component for the same elements of the array. The lines are marked AC and DC to differentiate the two plots. According to this simulation, a vessel (specifically, a blood vessel) is disposed between the light sensor array and a light emitter array, with the vessel located generally between the light emitter array and the light sensor array in the region between 40 and 180 pixels.

As illustrated in FIG. 6, the DC signal plot decreases from a relatively high value to a considerably lower value, and then increases from the lower value back to higher value at two different points (i.e., at points 300, 302) along the sensor array 112. In accordance with the observations made above, the decrease in the magnitude of the DC signal in the region would be expected to occur where the vessel is disposed between the light emitter 110 and the light sensor 112, and it therefore may be inferred that the vessel V is disposed between the point at which the DC signal plot transitions from the higher value to the lower value (i.e., point 300) and the point at which the DC signal plot transitions from the lower value back to the higher value (i.e., point 302).

In addition, the AC signal increases significantly from a relatively low value to a higher value at the point (i.e., point 304) on one side of where the vessel is presumably located, and from a high value to a lower value (i.e., point 306) on the other side of where the vessel is located. As also mentioned above, the relative increase in pulsatile (AC) signal is believed to occur where the vessel is disposed between the light emitter 110 and the light sensor 112, and it therefore may be inferred that the vessel V is disposed between the point at which the AC signal plot transitions from the lower value to the higher value (i.e., point 304) and the point at which the AC signal plot transitions from the higher value back to the lower value (i.e., point 306).

While either the change in the DC signal or the change in the AC signal may be used to define a region of interest (ROI), the combination of the information on the transitions in the AC signal may be combined with the transitions in the DC signal to define an ROI to which the further consideration of the pulsatile (AC) information is confined. That is, the system 100 (and more particularly the controller 120) may consider a subset of elements of all of the elements of the sensor array 112 in accordance with this information. This may be particularly helpful in eliminating fluctuations unrelated to the vessel in individual sensors along the array. According to such embodiments, the transitions between higher and lower values for each of the DC and AC plots are determined, and only the ROI where there is overlap between decreased DC magnitude and increased AC magnitude is considered. As illustrated in FIG. 6, this region would be between the vertical bars (i.e., from about 40 pixels to 180 pixels).

According to embodiments of the present disclosure, as illustrated in FIGS. 4 and 5, the resting diameter of the vessel may be calculated based on a correlation observed between the expanded outer diameter of the vessel and the inner diameter of the vessel. In particular, it has been observed that the resting diameter of the vessel correlates to the average of the expanded outer diameter of the vessel and the inner diameter of the vessel. To perform this calculation, the expanded outer diameter (or line A) of the vessel is determined to be the distance between a first pair of points at which the AC magnitude is approximately 50% of the peak AC magnitude: the leftmost occurrence (i.e., point 312) prior to (or leading) the leftmost AC peak magnitude (i.e., at point 308) and the rightmost occurrence (i.e., point 314) after (or lagging) the rightmost AC peak magnitude (i.e., at point 310). In addition, the inner diameter (or line C) is determined to be the distance between a second pair of points at which the AC magnitude is approximately 50% of the peak AC magnitude: the leftmost occurrence (i.e., point 316) after (or lagging) the leftmost AC peak magnitude (i.e., at point 308) and the rightmost occurrence (i.e., point 318) prior to (or leading) the rightmost AC peak magnitude (i.e., at point 310). These distances may also be described as the distances between the two occurrences of 50% peak AC magnitude outside and inside the peak AC magnitudes. It may also be said that the second pair is disposed between or inside the first pair.

It is not necessary to use the occurrences at 50% peak AC magnitude according to all embodiments of the present disclosure. According to other embodiments, the inner diameter may be determined to be distance between the leftmost occurrence after (or lagging) the leftmost AC peak magnitude and the rightmost occurrence prior to (or leading) the rightmost AC peak magnitude of 5% peak AC magnitude, while the expanded outer diameter also was determined at the 5% peak AC magnitude occurrences described above.

Finally, as illustrated in FIG. 6, the resting outer diameter (line B) may be determined to be the average between the inner diameter (line C) and the expanded outer diameter (line A).

Figure 7:
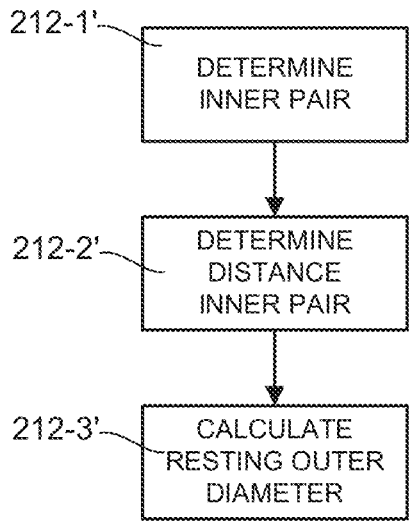
FIG. 7 is a flow diagram of alternate actions that may be performed as part of the method illustrated in FIG. 4.

According to other embodiments of the present disclosure, the determination of the resting outer diameter of the vessel V may be calculated without reference to two pairs of positions along the row of light sensors. More particular, the actions performed by the system 100 at the block 212 of the method 200 of FIG. 4 to determine the resting outer diameter of the vessel V may be as illustrated in FIG. 7. According to this alternate method, the action of block 212 may include determining a pair of positions along the row of light sensors at block 212-1' in between the two positions where the peak magnitudes occur. The single pair of positions (or "inner" pair) may occur where the magnitudes of the pulsatile component are a percentage of the first (or second) peak magnitude. For example, the inner pair may be defined by the pair of positions between the positions where the peak magnitudes occur corresponding to 50% of the first (or second) peak magnitude. In addition, the action of block 212 may include determining a distance between the inner pair at block 212-2'.

At block 212-3', the distance between the inner pair of positions is then used to calculate the resting outer diameter. According to this method, as was the case in the method of FIG. 5, the distance between the inner pair of positions is representative of the inner diameter of the vessel V. Further, it believed that the inner diameter of a vessel undergoing expansion and contraction varies to a far lesser degree (if at all) than the outer diameter. Moreover, it has been observed that the signal from the edges of the vessel may be obscured by the presence of tissue disposed about the vessel. Consequently, rather than attempting to approximate the outer diameter of the vessel, a relationship may be determined empirically between the inner diameter and resting outer diameter, which relationship may be used to calculate the resting outer diameter based on the measurement of the inner diameter, as determined in accordance with the actions of blocks 212-1' and 212-2'.

Figure 8:
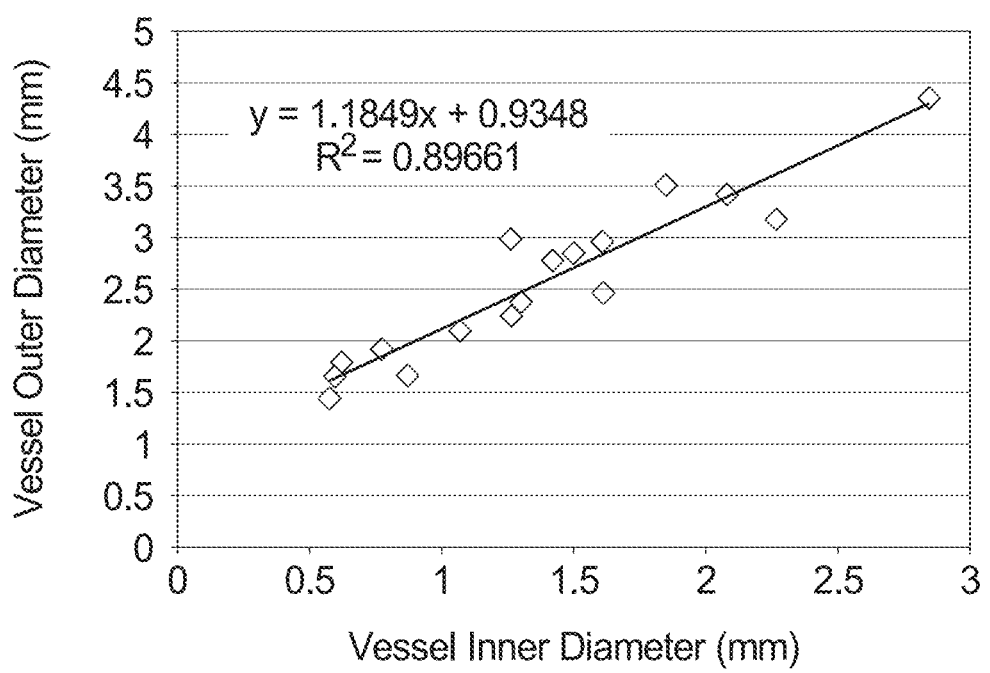
FIG. 8 is a graph comparing the outer diameters of various porcine arteries relative to the inner diameters of these arteries.

In its simplest form, the resting outer diameter may be determined to be a multiple of the inner diameter. According to other embodiments, the resting outer diameter may be calculated to be a multiple of the inner diameter with the addition of a constant term. FIG. 8 is a graph comparing the inner diameters and resting outer diameters of a set of muscular arteries. Based on this graph, a formula relating the outer diameter (y) with the inner diameter (x) was determined ($y=1.2x+0.9$). Accordingly, for a given inner diameter determined at blocks 212-1' and 212-2', the formula may be used to calculate the resting outer diameter at block 212-3'

Figure 9:
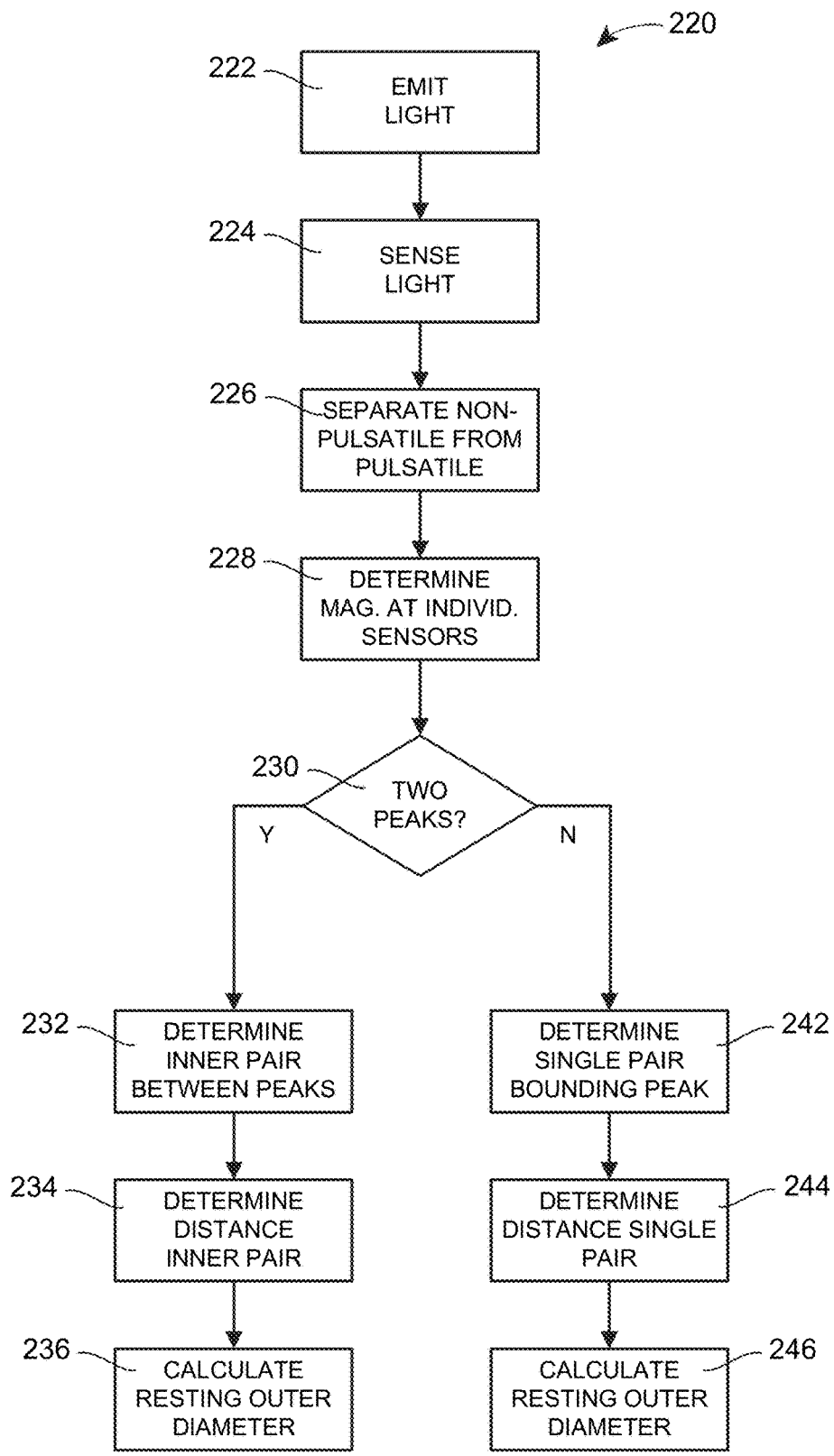
FIG. 9 is a flow diagram of a method according to an alternate embodiment of the present disclosure, which method may be carried out using the system of FIG. 1.

A further embodiment of a method that may be practiced using, for example, the system 100 illustrated in FIG. 1 is illustrated in FIG. 9. The method 220 illustrated in FIG. 9 addresses a complication that may occur if the vessel is grasped tightly between the jaws of an instrument, such as is illustrated in FIGS. 1 and 2. In particular, the compression of the vessel V between the jaws of the surgical instrument 106 may change the pulsatile component of the signal, such that only a single peak may be observed, instead of the two peaks as illustrated in FIG. 6.

The method 220 is similar to the method 200 in that light is emitted from the light emitter 110 at block 222, and the transmitted light is sensed or detected by the light sensor array 112 at block 224. The system 100 (or more particularly the controller 114) operates to separate the non-pulsatile component of the signal from the pulsatile component of the signal at block 226, and determines the magnitude of the pulsatile component at the individual sensors at block 228.

At block 230, the system 100 (controller 114) then makes a determination as to the number of positions identified with a peak pulsatile magnitude at block 230. According to certain embodiments, this determination may be performed after a region of interest is identified using transitions in the non-pulsatile component (e.g., from a higher magnitude to a lower magnitude) and optionally in the pulsatile component (e.g., from a lower magnitude to a higher magnitude). In fact, according to some embodiments, the determination at block 230 is performed once the transition in the non-pulsatile component of the signal from a higher magnitude to a lower magnitude is identified.

If the determination is made at block 230 that two peaks are present, for example, then the method 220 may proceed to blocks 232, 234, 236, where a method similar to that described in regard to FIG. 7 is performed (although it will be appreciated that a method similar to that described in regard to FIG. 5 may be substituted). If the determination is made at block 230 that a single peak is present, then the method 220 may proceed to blocks 242, 244, 246. In particular, a determination is made at block 242 as to a single pair of positions along the row of light sensors where the magnitudes of the pulsatile component are a percentage of the peak magnitude. For example, the pair may be defined by the pair of positions on either side of the peak magnitude (i.e., to the left or the right of the position corresponding to the peak magnitude) where the magnitude corresponds to 50% of the peak magnitude. In addition, the system 100 (controller 114) may determine the distance between this pair of positions at block 244. The system 100 may then use the distance determined as the value for the inner diameter, and calculate the resting outer diameter using the relationship established between inner diameter and outer diameter, in a process similar to that described in regard to block 212-3' in FIG. 7.

It will be recognized that while the method 220 was described with reference to a determination as to how many peaks are present, the specifics as to how this determination is performed may differ among the various embodiments. For example, the determination may be made according to whether one peak is or two peaks are present. Alternatively, the determination may be made according to whether a single peak is present, with subsequent actions taken dependent upon whether the answer to this question is yes or no.

Figure 10:
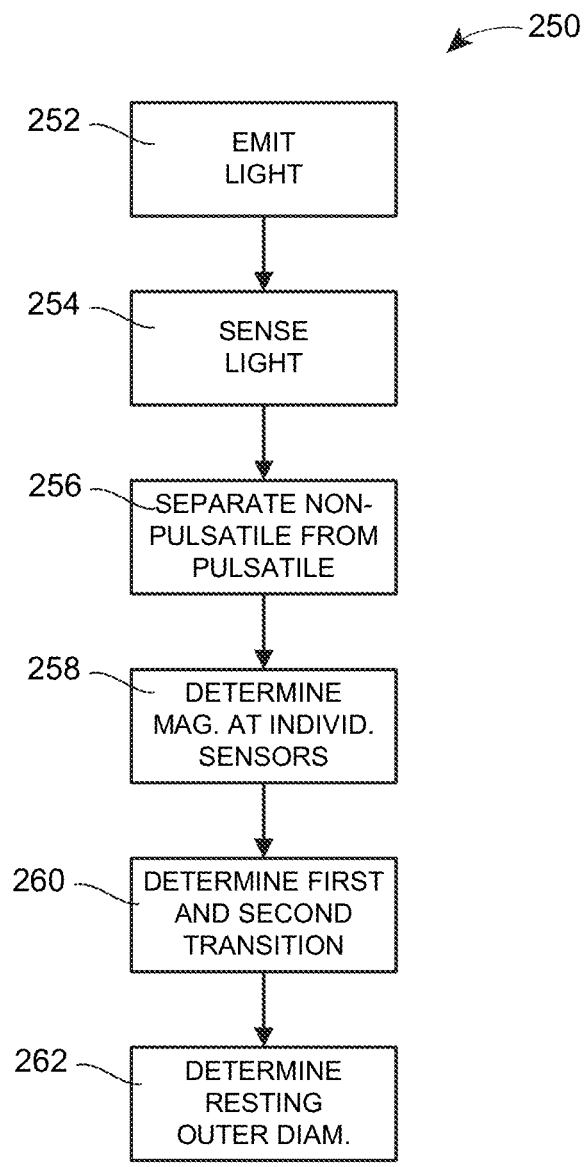
FIG. 10 is a flow diagram of a method according to a further alternate embodiment of the present disclosure, which method may be carried out using the system of FIG. 1.

A further alternative to the methods described in FIGS. 4-9 is to use the non-pulsatile component of the signal to determine the vessel outer diameter. As illustrated in FIG. 10, the method 250 starts much like the methods 200, 220, in that light is emitted at block 252, transmitted light is sensed or detected at block 254, and pulsatile and non-pulsatile components are separated at block 256. Unlike the methods above, the system 100 (controller 114) interrogates the non-pulsatile component at block 258 to determine the non-pulsatile magnitude at individual sensors at block 258. Moreover, unlike the methods above, the system 100 determines the positions along the row of light sensors where the non-pulsatile magnitude transitions from a higher value to a lower value and where the non-pulsatile magnitude transitions from a lower value back to a higher value at block 260. This pair of positions, based on these transitions in the non-pulsatile component of the signal, is then used to determine the resting outer diameter at block 262. For example, the distance between the pair of positions may be used as the estimate for the resting outer diameter, or a relationship based on empirical data may be used to calculate the resting outer diameter according to the distance between the pair of positions where the non-pulsatile component transitions.

Further enhancements may be included in the above embodiments, or may be practiced separately in combination to provide a further embodiment of a method for use with the surgical system 100.

For example, relative to the detection of the region of interest, the contrast of the DC profile may be used to determine the presence of the region wherein the DC profile decreases and then increases (i.e., "dips"). According to this method, the contrast of the DC profile is defined as:

$$1-(\min_{1 \leq j \leq N} DC_j / \max_{1 \leq j \leq N} DC_j) \quad \text{(Eqn.)}$$

where N=the total number of sensors.

The region of interest may then be determined using the first order derivative.

Figure 11:
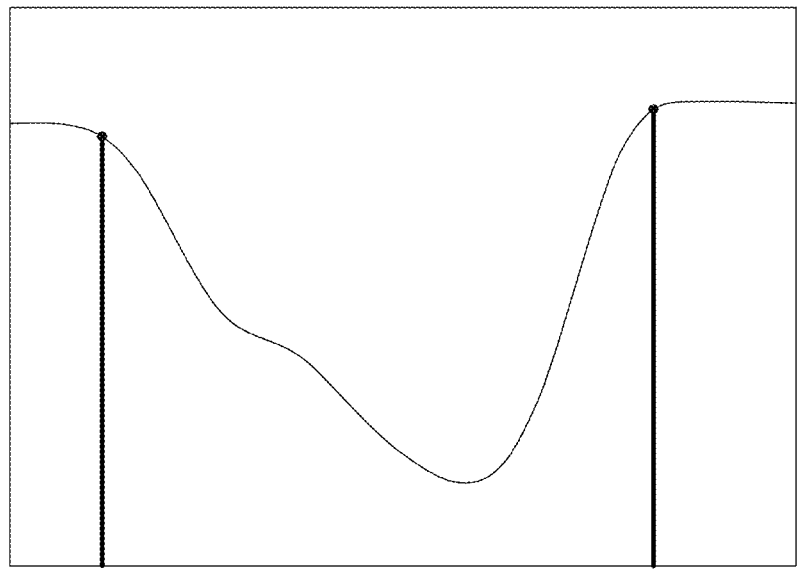
FIG. 11 is a graph of the magnitude of the non-pulsatile (DC) component for each of the elements of light sensor array before mirroring.
Figure 12:
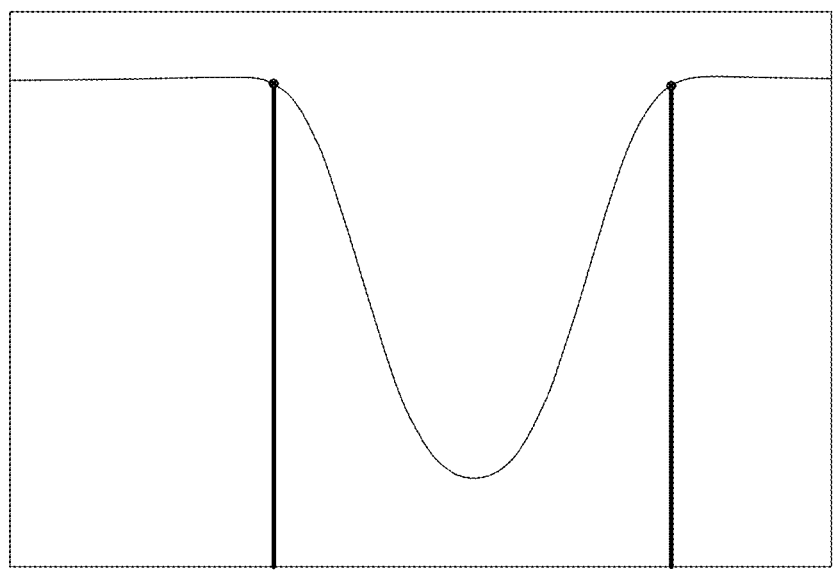
FIG. 12 is the graph of FIG. 11 corrected to provide an ideal region of interest using mirroring.

Furthermore, mirroring may be used to extract the "ideal" region of interest. It is believed that mirroring can be useful in this setting because vessels, such as arteries, can be expected to be symmetrical in structure. Thus, while the DC profile may not follow the symmetry of the vessels because tissue of differing thickness is disposed about the vessels, this expectation that the DC profile should be symmetrical can be used to improve the accuracy of at least the vessel size determination. See FIGS. 11 and 12.

In addition, the DC profile may be used to adapt the intensity emitted by the light emitter 110. In particular, it is believed that the intensity of the light emitter 110 plays an important role in the accuracy of vessel detection and vessel size determination. If the intensity of the light emitter 110 is set too low, the light may be absorbed by the tissue before reaching the sensor 112. In such a circumstance, the sensor 112 may not be able to detect the pulsatile nature of the vessel, and it may be difficult to differentiate the vessel (e.g., artery) from the surrounding tissue (i.e., low resolution). On the other hand, if the intensity of the light emitter is set too high, only the portion of the sensor 112 located in the very center of the vessel may experience the decrease in non-pulsatile (DC) signal, which leasing to error in determining the region of interest and other spatial characteristics of the vessel. Therefore, it would be desirable to provide a method and mechanism for selection of the intensity of the light emitter 110 that would limit the consequences of using an intensity that was either too low or too high for conditions.

Figure 13:
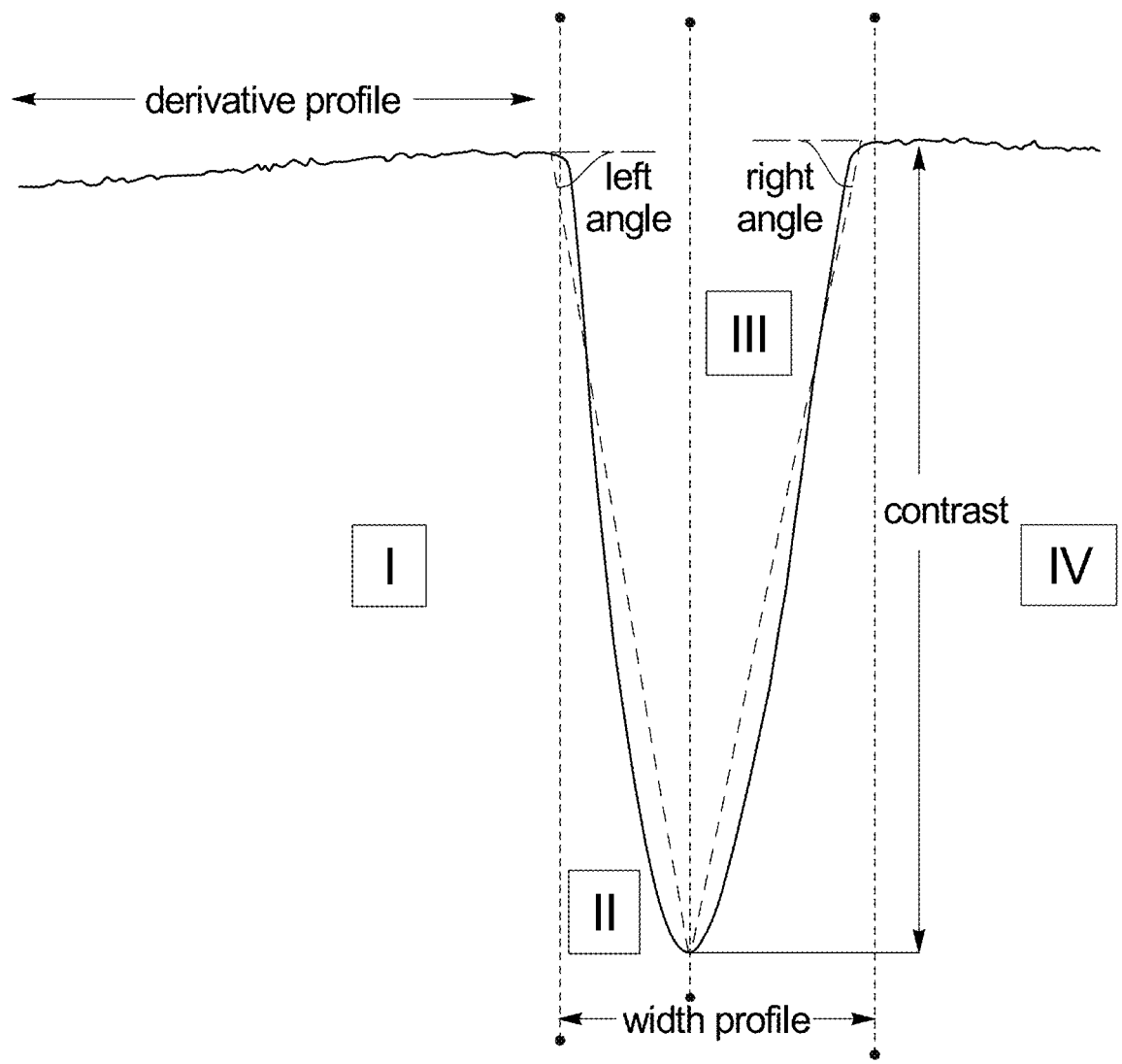
FIG. 13 is a graph of an exemplary DC profile used to discuss method of adapting the light intensity emitted by the light emitter.

FIG. 13 illustrates an exemplary DC profile that will be used to discuss the various profile parameters that may be used to adapt the light emitter intensity such that it is neither too low nor too high for a particular setting. It will be recognized that the DC profile illustrated in FIG. 13 has four separate regions, labeled with Roman numerals I, II, III, and IV. Certain profile parameters are analyzed within regions I and IV, while other parameters are analyzed within regions II and III.

In particular, within regions I and IV, the relevant parameter is the derivative profile, while within regions II and III, the relevant parameters are the left and right angles, the contrast, the width profile and the symmetry. While the derivative profile is self-explanatory, it will be recognized that the left and right angles are determined using a straight line drawn from the point at which the derivative profile changes to a non-zero value (beginning of the "dip") to the lowest DC value (the bottom of the "dip") and as measured relative to the horizontal as illustrated in FIG. 13, and the width profile is the distance between the left-hand edge (as viewed in FIG. 13) of the "dip" to the right-hand edge. The contrast is determined using the equation provided above. In addition, a further parameter, referred to as the contrast to width ratio (CWR), may be determined by taking the ratio of the contrast to the width profile.

Starting with the derivative profile in regions I and IV, it is believed that when the emitter light intensity is neither too low nor too high, the derivative profile will be approximately zero in regions I and IV. Furthermore, it is believed that the left and right angles should be in the range of 45 to 65 degrees. It is also believed that the contrast should be within the range of 0.4 to 0.6, and the width profile should not be too small nor too broad. In particular, it is believed that the CWR should be approximately 1 when the intensity Is neither too low nor too high. It is also believed that the profile should exhibit a relatively uniform symmetry between regions II and III, which may be quantified as a ratio of the width of the profile in region II to the width of the profile in region III. Here as well, it is believed the ratio should be approximately 1 when the intensity is neither too low nor too high.

Figure 14:
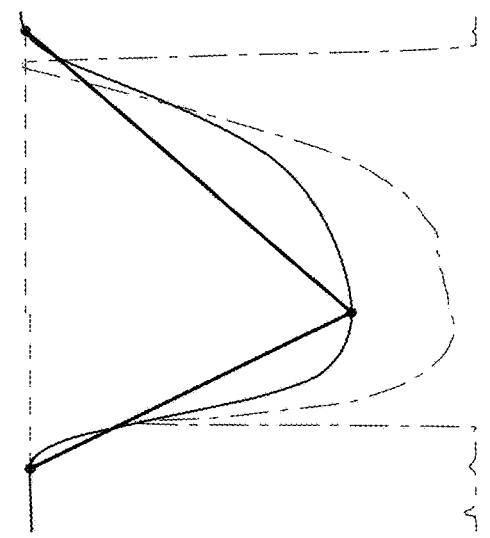
FIGS. 14-16 are graphs of DC profiles at different light intensities.
Figure 15:
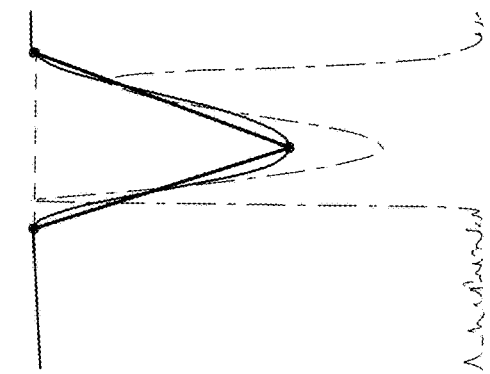
Figure 16:
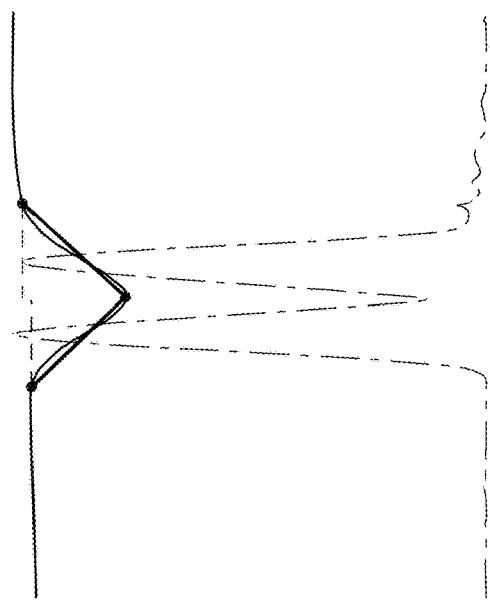

FIGS. 14-16 illustrate a series of DC profiles and AC profiles (DC profiles in solid line and AC profiles in dotted solid line) at different light intensities for the light emitter 110. In all of the illustrations, the lines used to calculate the left and right angles have been added, although the regions I, II, III and IV have not been marked as such. However, one may easily determine the regions in FIGS. 14-16 based on the presence of these lines. FIG. 14 illustrates a situation where the intensity of the light emitter was selected to be too low for conditions, while FIG. 15 illustrates a situation where the intensity of the light emitter was selected too high for conditions. On the other hand, FIG. 16 illustrates a situation where the intensity of the light emitter had been adapted to improve the determination of the size of the vessel.

Under certain circumstances, enhancements used generally with the DC profile may be used in conjunction with these parameters when adapting the light intensity of the light emitter. For example, mirroring may be used in conjunction with the other parameters when using the DC profile to adapt the light intensity of the light emitter 110.

Figure 17:
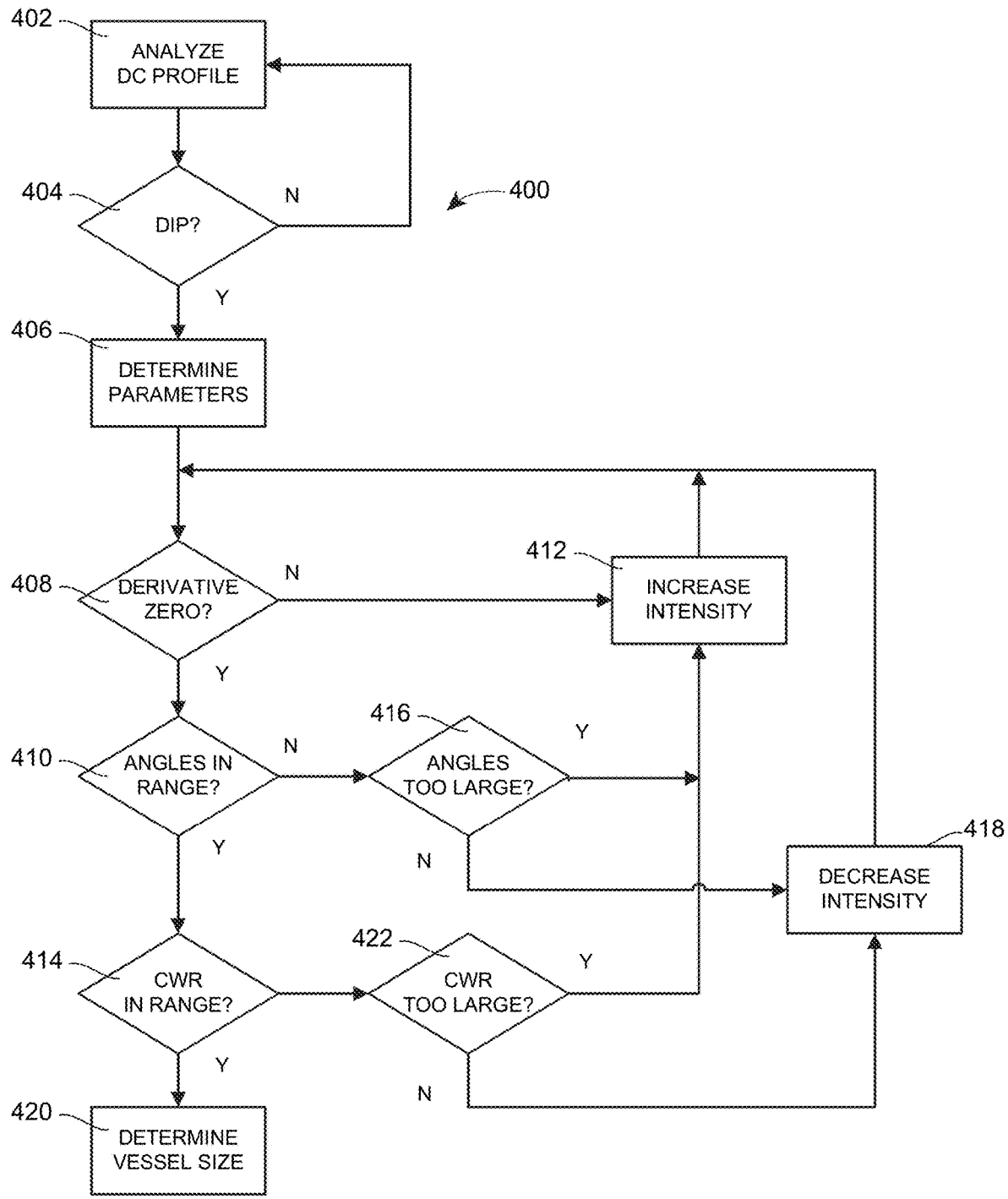
FIG. 17 is a flow diagram of a method using the parameters of the DC profile to adapt the light intensity emitted by the light emitter to limit vessel size determination error.

One method 400 using the above parameters to adapt the light intensity is illustrated in FIG. 17. The DC profile is analyzed at block 402 for the presence of a dip in the DC profile. A determination is made at block 404 whether a dip is present, or not. If the determination is made at block 404 that the dip is present, the method 400 continues to block 406; if not, the method 400 returns to block 402.

At block 406, the parameters discussed above are determined for the DC profile, and a series of comparisons are made relative to the ranges also discussed above. For example, at block 408, a determination is made whether the derivative profile in regions I and IV are approximately zero. If the derivative profile is approximately zero, the method 400 continues to the determination at block 410; if the derivative profile is not approximately zero, the light intensity is increased at block 412, and the method 400 returns to block 408.

At block 410, a determination is made whether the left and right angles are within range. If the angles are within range, the method 400 proceeds to block 414. If the angles are not within range, a subsequent determination is made at block 416 whether the angles fall outside the range because they are too large. If the angles are too large, then the method 400 proceeds to block 412 and the light intensity is increased; if the angles are outside the range because they are not too large (i.e., they are too small), then the method 400 proceeds to block 418 and the light intensity is decreased.

If the method 400 proceeds to block 414, a determination is made whether the contrast to width ratio is approximately 1. If the CWR is approximately 1, then the method 400 proceeds to block 420 where the vessel size is determined. If the CWR is not approximately 1, then the method 400 proceeds to block 422 where a determination is made whether the CWR is too large. If the CWR is too large, the light intensity is increased at block 412 and the method 400 returns to block 408; if the CWR is not too large, the light intensity is decreased at block 418, and the method 400 returns to block 408.

Having thus described the surgical system 100, the method 200 and the principles of the system 100 and the method 200 in general terms, further details of the system 100 and its operation are provided.

Initially, while the emitter 110 and the sensor 112 are described as disposed at the working end 104 of the surgical instrument 106, it will be recognized that not all of the components that define the emitter 110 and the sensor 112 need be disposed at the working end of the instrument 106. That is, the emitter 110 may comprise a light emitting diode, and that component may be disposed at the working end 104. Alternatively, the emitter 110 may include a length of optical fiber and a light source, the source disposed remotely from the working end 104 and the fiber having a first end optically coupled to the source and a second end disposed at the working end 104 facing the sensor 112. According to the present disclosure, such an emitter 110 would still be described as disposed at the working end 104 because the light is emitted into the tissue at the working end 104 of the instrument 106. A similar arrangement may be described for the sensor 112 wherein an optical fiber has a first end disposed facing the emitter 110 (or perhaps more particularly, an end of the optical fiber that in part defines the emitter 110) and a second end optically coupled to other components that collectively define the sensor 112.

As also mentioned above, the light emitter 110 and light sensor 112 are positioned opposite each other. This does not require the emitter 110 and the sensor 112 to be directly facing each other, although this is preferred. According to certain embodiments, the emitter 110 and sensor 112 may be formed integrally (i.e., as one piece) with jaws 180 of a surgical instrument 106. See FIGS. 1 and 2. In this manner, light emitted by the emitter 110 between the jaws 180 and through the tissue of interest may be captured by the light sensor 112.

The light emitter 110 may include one or more elements. According to an embodiment schematically illustrated in FIG. 2, the light sensor 112 may include a first light emitter 110-1, a second light emitter 110-2, and a third light emitter 110-3. All of the light emitters may be adapted to emit light at a particular wavelength (e.g., 660 nm), or certain emitters may emit light at different wavelengths than other emitters.

As to those embodiments wherein the light emitter 110 is in the form of an array including one or more light emitting diodes, as is illustrated in FIG. 2 for example, the diodes may be arranged in the form of a one-dimensional, two-dimensional or three-dimensional array. An example of a one-dimensional array may include disposing the diodes along a line in a single plane, while an example of a two-dimensional array may include disposing the diodes in a plurality of rows and columns in a single plane. Further example of a two-dimensional array may include disposing the diodes along a line on or in a curved surface. A three-dimensional array may include diodes disposed in more than one plane, such as in a plurality of rows and columns on or in a curved surface.

The light sensor 112 according to the embodiments of the present disclosure also includes one or more individual elements. According to an embodiment illustrated in FIG. 2, the light sensor 112 may include a first light sensor 112-1, a second light sensor 112-2, an n-th light sensor 112-n, and so on. As was the case with the light emitters 110-1, 110-2, 110-3, the light sensors 112-1, 112-2, 112-3 may be arranged in an array, and the discussion in regard to the arrays above applied with equal force here.

As discussed above, the system 100 may include hardware and software in addition to the emitter 110, sensor 112, and controller 114. For example, where more than one emitter 110 is used, a drive controller may be provided to control the switching of the individual emitter elements. In a similar fashion, a multiplexer may be provided where more than one sensor 112 is included, which multiplexer may be coupled to the sensors 112 and to an amplifier. Further, the controller 114 may include filters and analog-to-digital conversion as may be required.

Figure 18:
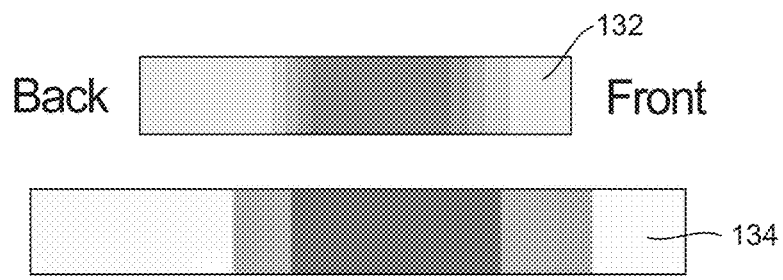
FIG. 18 is a simulated partial screen capture of a video monitor used in the system of FIG. 1.

As for the indicator 130 used in conjunction with controller 114, a variety of output devices may be used. As illustrated in FIG. 1, a light emitting diode 130-1 may be attached to or incorporated into the associated surgical instrument 106, and may even be disposed at the working end 104 of the instrument 106. Alternatively or in addition, an alert may be displayed on a video monitor 130-2 being used for the surgery, or may cause an image on the monitor to change color or to flash, change size or otherwise change appearance. For example, FIG. 18 illustrates a portion of a graphical user interface (GUI) that may be displayed on the video monitor 130-2, wherein a first region 132 is representative of the location of a section of a vessel and surrounding tissue between the jaws of the surgical instrument 106 and a second region 134 is an enhanced representation of the section of vessel and surrounding tissue illustrated in first region 132 with the vessel represented in a contrasting fashion to the surrounding tissue (e.g., through the use of bands of different color for the vessel and the surrounding tissue). The indicator 130 may also be in the form of or include a speaker 130-3 that provides an auditory alarm. The indicator 130 also may be in the form of or may incorporate a safety lockout 130-4 associated with the surgical instrument 106 that interrupts use of the instrument 106. For example, the lockout could prevent ligation or cauterization where the surgical instrument 106 is a thermal ligature device. As a still further example, the indicator 130 also may be in the form of a haptic feedback system, such as a vibrator 130-5, which may be attached to or formed integral with a handle or handpiece of the surgical instrument 106 to provide a tactile indication or alarm. Various combinations of these particular forms of the indicator 130 may also be used.

As mentioned above, the surgical system 100 may also include the surgical instrument 106 with the working end 104, to which the light emitter 110 and light sensor 112 are attached (in the alternative, removably/reversibly or permanently/irreversibly). The light emitter 110 and the light sensor 112 may instead be formed integrally (i.e., as one piece) with the surgical instrument 106. It is further possible that the light emitter and light sensor be attached to a separate instrument or tool that is used in conjunction with the surgical instrument or tool 106.

As noted above, the surgical instrument 106 may be a thermal ligature device in one embodiment. In another embodiment, the surgical instrument 106 may simply be a grasper or dissector having opposing jaws. According to still further embodiments, the surgical instrument may be other surgical instruments such as surgical staplers, clip appliers, and robotic surgical systems, for example. According to still other embodiments, the surgical instrument may have no other function than to carry the light emitters/light sensors and to place them within a surgical field. The illustration of a single embodiment is not intended to preclude the use of the system 100 with other surgical instruments or tools 106.

EXAMPLES

Experiments have been conducted using an embodiment of the above-described system. The experiments and results are reported below.

The first set of experiments was conducted using an excised porcine carotid artery. To simulate the pulsatile flow of fluid found in such blood vessels, a submersible DC pump was used. The pump was capable of operation at between 40 and 80 cycles per minute, and could provide a flow rate that could be set to a particular value. The fluid used was bovine whole blood to which heparin had been added and that was maintained at an elevated temperature to maintain physiological viscosity. For the experiments described below, the blood was pumped at 60 cycles per minute and at a flow rate of 500 mL per minute.

Figure 19:
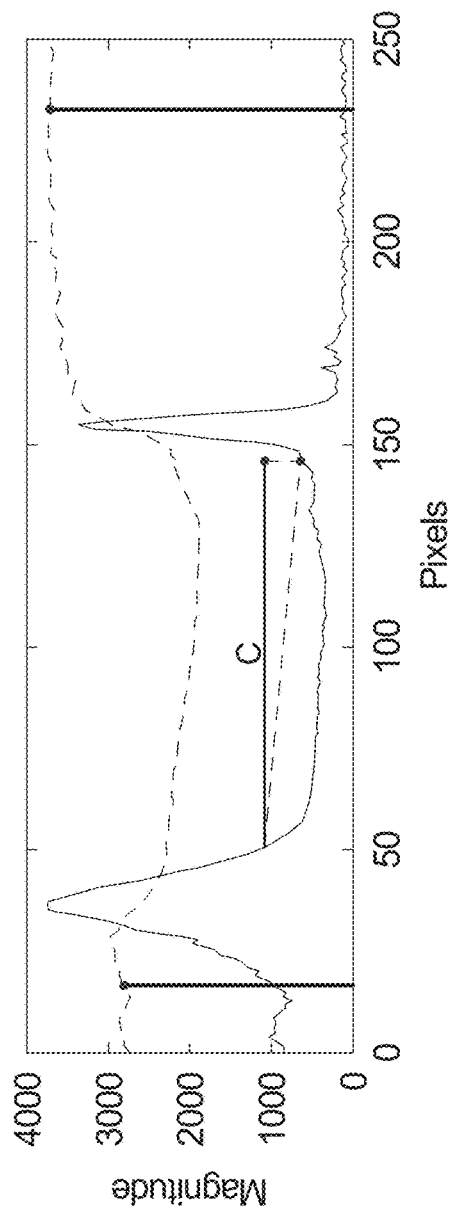
FIG. 19 is a graph of the magnitudes of the pulsatile (AC) and non-pulsatile (DC) components for each of the elements (pixels) of a light sensor array (linear CCD array) used in a first set of experiments.

A light emitter array was disposed opposite a light sensor array with the excised porcine carotid artery disposed therebetween. The light emitter array included five light emitting diodes that emitted light at 660 nm. The light sensor array included a linear CCD array composed of 250 elements arranged side-by-side, with each group or set of 20 elements fitting into 1 mm of contiguous space along the array. The system was operated for 10 seconds, with the results of the experiments plotted in FIG. 19. The inner diameter of the vessel was determined by using the distance between a pair of positions where the magnitude of the pulsatile component was 50% of the peak magnitude (i.e., line C in FIG. 19).

Figure 20:
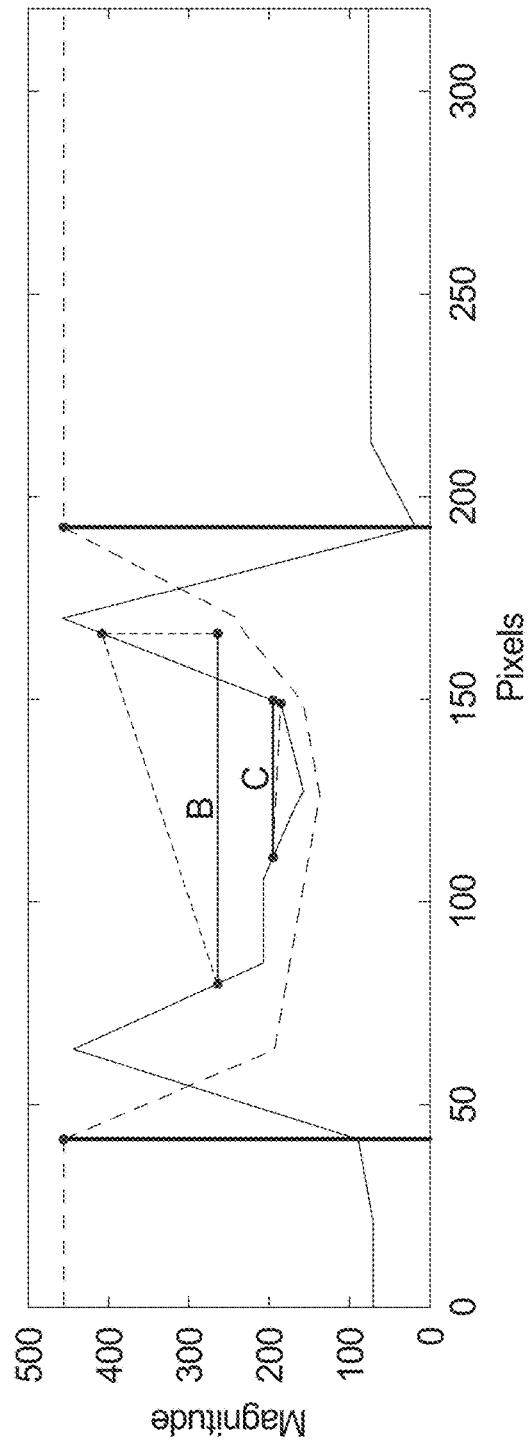
FIG. 20 is a graph of the magnitudes of the pulsatile (AC) and non-pulsatile (DC) components for each of the elements of a light sensor array (photodetector array, with measurements presented in pixels for comparison with FIG. 19) used in a second set of experiments.

The second set of experiments was conducted using a light emitter array opposite a light sensor array, with the porcine carotid artery of a living porcine subject disposed therebetween. The light sensor array included five light emitting diodes that emitted light at 660 nm. The light sensor array included 16 individual photodetector elements, each element being 0.9 mm wide. The elements were spaced with 0.1 mm between adjacent elements, such that each element occupied 1 mm of contiguous space along the array. The system was operated for 15 seconds, with the results of the experiment plotted in FIG. 20. The measurements for each photodetector were interpolated and converted to pixels to permit a comparison between the first set of experiments and the second set of experiments. Again, the inner diameter of the vessel was determined by using the distance between a pair of positions where the magnitude of the pulsatile component was 50% of the peak magnitude (i.e., line C in FIG. 20).

In both sets of experiments, the inner diameters of the porcine arteries determined using embodiments of the disclosed system were within a millimeter of the gross diameter measurements of the vessel. For example, relative to the first set of experiments, the inner diameter determined using the embodiment of the system was 4.7 mm, while the gross diameter measurement was 4.46 mm. As to the second set of experiments, the inner diameter determined using the embodiment of the system was 1.35 mm, and the gross diameter measurement was 1.1 mm.

For a third set of experiments, an embodiment of the system including an LED array emitting at 940 nm and a linear CCD array was used. The system was used to determine the resting outer diameters of four different arteries (gastric, left renal, right renal, and abdominal) in a living porcine subject. The system was operated for 10 seconds, and the inner diameters were determined using a pair of points associated with 50% of the peak magnitude. After using the system to determine the inner diameters, the arteries were excised and the gross vessel diameters were obtained by quantifying the cross-section of the vessels at the point of measurement along the vessels using NIH ImageJ software.

Figure 21:
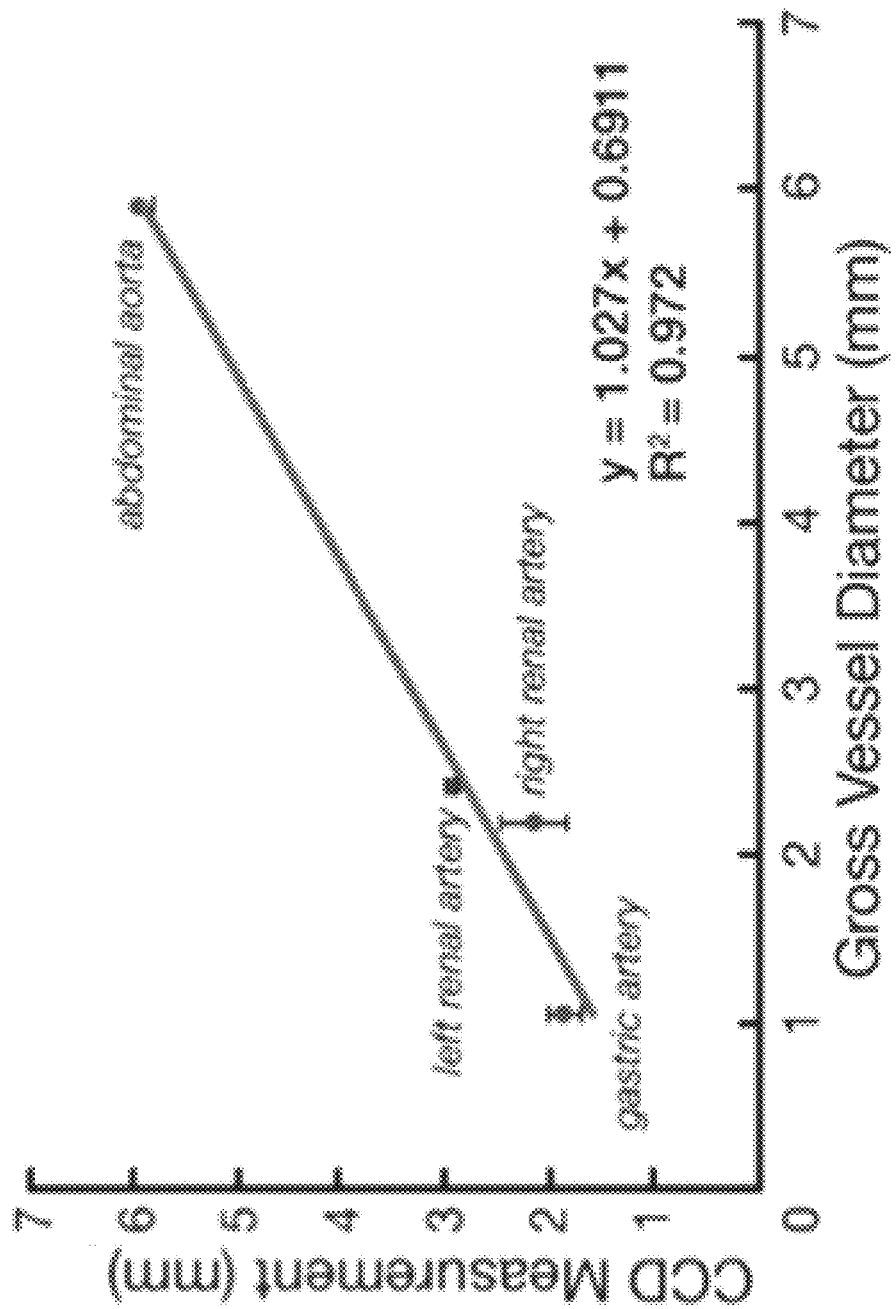
FIG. 21 is a graph comparing the inner diameters of various porcine arteries as determined using a light sensor array (linear CCD array) and as measured in a third set of experiments.

The results of the third group of experiments are illustrated in FIG. 21. As indicated in the graph, there is a close correlation between the inner diameters determined using an embodiment of the system disclosed herein and the inner diameters measured using conventional techniques. The error bars represent the standard deviation of measurements of the same artery taken at different points in time.

In conclusion, although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

What is claimed is:

1. A surgical system with an adaptable light intensity, comprising:
   at least one light emitter disposed at the working end of the surgical instrument, the at least one light emitter adapted to generate light at a first intensity;
   an array of light sensors disposed at the working end of the surgical instrument opposite the at least one light emitter, the array of light sensors comprising at least one row of light sensors, individual light sensors in the at least one row of light sensors each adapted to generate a signal comprising a non-pulsatile component with a magnitude; and
   a controller coupled to the array of light sensors, the controller comprising an analyzer configured to determine the magnitudes of the non-pulsatile components at the individual light sensors in the at least one row of light sensors, to determine if the non-pulsatile component transitions from a higher magnitude to a lower magnitude and from a lower magnitude to a higher magnitude, and if the non-pulsatile component transitions from a higher magnitude to a lower magnitude and from a lower magnitude to a higher magnitude, to determine if the first intensity should be changed to a second intensity, and to change the at least one light emitter to the second intensity, if so determined.

2. The surgical system according to claim 1, wherein the controller determines if the non-pulsatile component transitions from a higher magnitude to a lower magnitude or from a lower magnitude to a higher magnitude according to a derivative of a non-pulsatile profile for the array of light sensors.

3. The surgical system according to claim 2, wherein the controller determines if the first intensity should be changed to the second intensity in accordance with an angle determined using a first line drawn from a point along the non-pulsatile profile where the derivative changes from a zero value to a non-zero value to a point corresponding to the lowest non-pulsatile value, or using a second line drawn from a point along the non-pulsatile profile where the derivative changes from a non-zero value to a zero value to the point corresponding to the lowest non-pulsatile value.

4. The surgical system according to claim 3, wherein the controller determines if the angle is in a range from a first value to a second value, the second value being larger than the first value.

5. The surgical system according to claim 4, wherein the first value is approximately 45 degrees and the second value is approximately 65 degrees.

6. The surgical system according to claim 4, wherein if the angle is below the first value, the first intensity is decreased to the second intensity.

7. The surgical system according to claim 4, wherein if the angle is above the second value, the first intensity is increased to the second intensity.

8. The surgical system according to claim 1, wherein the analyzer determines the magnitudes of the non-pulsatile components at the individual light sensors in the at least one row of light sensors, determines a pair of positions corresponding to a first transition in the non-pulsatile component from a higher magnitude to a lower magnitude and a second transition in the non-pulsatile component from a lower magnitude to a higher magnitude, and determines a resting outer diameter of the vessel based on the pair of positions.

9. The surgical system according to claim 1, wherein the signal comprises a pulsatile component and the analyzer determines magnitudes of the pulsatile components at the individual light sensors in the at least one row of light sensors, determines a first peak magnitude and a second peak magnitude of the pulsatile components, and determines a resting outer diameter of the vessel based on the first peak magnitude and the second peak magnitude of the pulsatile components.

10. A method of adapting a light intensity, comprising:
    emitting light at the working end of the surgical instrument, the light emitted at a first intensity;

sensing light at the working end of the surgical instrument at an array of light sensors comprising at least one row of light sensors;

generating a signal comprising a non-pulsatile component with a magnitude for each individual light sensor in the at least one row of light sensors;

determining the magnitudes of the non-pulsatile components at the individual light sensors in the at least one row of light sensors;

determining if the non-pulsatile component transitions from a higher magnitude to a lower magnitude and from a lower magnitude to a higher magnitude; and if the non-pulsatile component transitions from a higher magnitude to a lower magnitude and from a lower magnitude to a higher magnitude, determining if the first intensity should be changed to a second intensity and changing to the second intensity, if so determined.

11. The method according to claim 10, wherein determining if the non-pulsatile component transitions from a higher magnitude to a lower magnitude or from a lower magnitude to a higher magnitude comprises determining according to a derivative of a non-pulsatile profile for the array of light sensors.

12. The method according to claim 11, wherein determining if the first intensity should be changed to a second intensity comprises determining in accordance with an angle determined using a first line drawn from a point along the non-pulsatile profile where the derivative changes from a zero value to a non-zero value to a point corresponding to the lowest non-pulsatile value, or using a second line drawn from a point along the non-pulsatile profile where the derivative changes from a non-zero value to a zero value to the point corresponding to the lowest non-pulsatile value.

13. The method according to claim 12, further comprising determining if the angle is in a range from a first value to a second value, the second value being larger than the first value.

14. The method according to claim 13, wherein the first value is approximately 45 degrees and the second value is approximately 65 degrees.

15. The method according to claim 13, wherein if the angle is below the first value, decreasing the first intensity to the second intensity.

16. The method according to claim 13, wherein if the angle is above the second value, increasing the first intensity to the second intensity.

17. The method according to claim 10, further comprising:

determining the magnitudes of the non-pulsatile components at the individual light sensors in the at least one row of light sensors, determining a pair of positions corresponding to a first transition in the non-pulsatile component from a higher magnitude to a lower magnitude and a second transition in the non-pulsatile component from a lower magnitude to a higher magnitude, and determining a resting outer diameter of the vessel based on the pair of positions.

18. The method according to claim 10, wherein the signal comprises a pulsatile component and further comprising:

determining magnitudes of the pulsatile components at the individual light sensors in the at least one row of light sensors, determining a first peak magnitude and a second peak magnitude of the pulsatile components, and determining a resting outer diameter of the vessel based on the first peak magnitude and the second peak magnitude of the pulsatile components.

19. A surgical system used to determine a size of a vessel within a region proximate to a working end of a surgical instrument, comprising:

at least one light emitter disposed at the working end of the surgical instrument;

an array of light sensors disposed at the working end of the surgical instrument opposite the at least one light emitter, the array of light sensors comprising at least one row of light sensors, individual light sensors in the at least one row of light sensors each adapted to generate a signal comprising a non-pulsatile component with a magnitude; and a controller coupled to the array of light sensors, the controller comprising an analyzer to determine the magnitudes of the non-pulsatile components at the individual light sensors in the at least one row of light sensors, to determine a pair of positions corresponding to a first transition in the non-pulsatile component from a higher magnitude to a lower magnitude and a second transition in the non-pulsatile component from a lower magnitude to a higher magnitude, and to determine a resting outer diameter of the vessel based on a symmetrical non-pulsatile profile according to the pair of positions.

* * * * *